United States Patent
Enoki et al.

(10) Patent No.: US 10,982,292 B2
(45) Date of Patent: Apr. 20, 2021

(54) **MARKER ASSOCIATED WITH ANTHRACNOSE RESISTANCE IN PLANT OF THE GENUS *FRAGARIA* AND USE THEREOF**

(71) Applicant: TOYOTA JIDOSHA KABUSHIKI KAISHA, Toyota (JP)

(72) Inventors: Hiroyuki Enoki, Hamamatsu (JP); Satoru Nishimura, Nagoya (JP); Momoe Suito, Toyohashi (JP); Tsukasa Nunome, Tsu (JP); Yuji Noguchi, Tsu (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 182 days.

(21) Appl. No.: 14/917,045

(22) PCT Filed: Sep. 5, 2014

(86) PCT No.: PCT/JP2014/073460
§ 371 (c)(1),
(2) Date: Mar. 7, 2016

(87) PCT Pub. No.: WO2015/034040
PCT Pub. Date: Mar. 12, 2015

(65) Prior Publication Data
US 2016/0201145 A1    Jul. 14, 2016

(30) Foreign Application Priority Data

Sep. 9, 2013  (JP) .............................. JP2013-186688
Aug. 15, 2014  (JP) .............................. JP2014-165405

(51) Int. Cl.
| | | |
|---|---|---|
| *C12Q 1/68* | (2018.01) | |
| *A01H 5/08* | (2018.01) | |
| *C12Q 1/6895* | (2018.01) | |
| *A01H 6/74* | (2018.01) | |

(52) U.S. Cl.
CPC ............. *C12Q 1/6895* (2013.01); *A01H 5/08* (2013.01); *A01H 6/7409* (2018.05); *C12Q 2600/13* (2013.01); *C12Q 2600/156* (2013.01)

(58) Field of Classification Search
None
See application file for complete search history.

(56) References Cited

U.S. PATENT DOCUMENTS

| | | |
|---|---|---|
| 2009/0222941 A1 | 9/2009 | Taguchi et al. |
| 2011/0154528 A1 | 6/2011 | Ragot et al. |

FOREIGN PATENT DOCUMENTS

| | | |
|---|---|---|
| JP | 2009-183224 A | 8/2009 |
| JP | 2010-516236 A | 5/2010 |
| WO | 2007/125958 A1 | 11/2007 |

OTHER PUBLICATIONS

Enoki et al. (Breeding research, 15(2), (Oct. 12, 2013) pp. 27-28).*
Iimura et al. (Breeding Research 15: pp. 90-97 (2012)) Concise English Translation Provided.*
Enoki et al. English translation.*
Iimura et al. English translation.*
Iimura et al. (Breeding Research 15: pp. 90-97 (2012), translation provided).*
Morgante et al. (Current Opinion in Biotechnology 2003, 14: pp. 214-219).*
Mauricio, 2001, Mapping Quantitative Trait Loci in Plants: Uses and Caveats for Evolutionary Biology, Nature Reviews Genetics 2: 370-381.*
Slate, 2005, Quantitative trait locus mapping in natural populations: progress, caveats and future directions, Molecular Ecology 14: 363-379.*
Enoki et al., "Construction of genetic linkage maps of cultivated strawberry using array marker technology and development of markers linked to anthracnose resistance gene", Breeding Research, 15(2) Oct. 12, 2013 (4 pages in total).
Sachiko N. Isobe et al., "Construction of an Integrated High Density Simple Sequence Repeat Linkage Map in Cultivated Strawberry (*Fragaria x ananassa*) and its Applicability", DNA Research, 2013, pp. 79-92, vol. 20.
K. Iimura, Tochigi Prefectural Agricultural Experiment Station, Abstracts of Research Results, 2011, pp. 51-52, No. 29.
Toyozo Sato et al., "Causal Fungi of Plant Anthracnose", Microbiol. Cult. Coll., 2009, pp. 27-32, vol. 25, No. 1.
Lerceteau-Köhler et al., "Identification of SCAR markers linked to Rca2 anthracnose resistance gene and their assessment in strawberry germplasm," Theor Appl Genet (2005) vol. 111, pp. 862-870.
Li et al., "Genome-wide identification and comparative expression analysis of NBS-LRR-encoding genes upon Colletotrichum gloeosporioides infection in two ectotypes of Fragaria vesca," Gene (2013) vol. 527, pp. 215-227.

* cited by examiner

*Primary Examiner* — Bratislav Stankovic
(74) *Attorney, Agent, or Firm* — Sughrue Mion, PLLC

(57) ABSTRACT

This invention is intended to develop many DNA markers in plants of the genus *Fragaria* and to evaluate anthracnose resistance with high accuracy with the use of such many DNA markers. The markers associated with anthracnose resistance in plants of the genus *Fragaria* each comprise a continuous nucleic acid region sandwiched between the nucleotide sequence as shown in SEQ ID NO: 1 and the nucleotide sequence as shown in SEQ ID NO: 10 in the chromosome of a plant of the genus *Fragaria*.

5 Claims, 22 Drawing Sheets

Specification includes a Sequence Listing.

Fig. 22

| Linkage group | Marker Name | Sachinoka | Parental Line Nou - 2 | F1 | | | | | | | |
|---|---|---|---|---|---|---|---|---|---|---|---|
| | | | | 1 | 2 | 3 | 4 | 5 | 6 | 7 | 8 |
| Parental Line Nou - 2 23rd linkage group | IA204069 | 529 | 1,216 | 1,352 | 417 | 1,370 | 2,141 | 570 | 1,770 | 532 | 621 |
| | IA204291 | 737 | 2,484 | 2,545 | 607 | 2,803 | 2,788 | 627 | 2,672 | 635 | 597 |
| | IA202531 | 593 | 2,695 | 2,997 | 402 | 3,008 | 4,755 | 511 | 4,864 | 492 | 448 |
| | IA200064 | 816 | 5,128 | 5,829 | 875 | 6,168 | 5,584 | 671 | 5,311 | 618 | 653 |
| | IA205184 | 515 | 3,408 | 3,727 | 422 | 3,553 | 3,069 | 460 | 2,565 | 490 | 451 |
| | IA202854 | 1,052 | 2,222 | 2,540 | 489 | 2,454 | 2,562 | 1,053 | 2,415 | 787 | 907 |
| | IA200826 | 457 | 13,950 | 15,663 | 386 | 17,189 | 21,362 | 412 | 20,572 | 417 | 407 |
| | IA202631 | 407 | 9,148 | 9,729 | 394 | 10,790 | 12,522 | 394 | 10,238 | 404 | 373 |
| | IA202517R* | 646 | 2,655 | 879 | 1,615 | 816 | 542 | 2,169 | 770 | 2,251 | 2,879 |
| | IA201502 | 417 | 13,076 | 13,283 | 463 | 13,848 | 17,816 | 427 | 15,042 | 412 | 401 |
| Rate of the strains exhibiting wilting or firing (%) | | 60.0 | 20.0 | 20.0 | 85.0 | 13.3 | 8.3 | 73.3 | 0.0 | 73.3 | 73.3 |

SEQUENCE LISTING

<160> NUMBER OF SEQ ID NOS: 32

<210> SEQ ID NO 1
<211> LENGTH: 220
<212> TYPE: DNA
<213> ORGANISM: Fragaria x ananassa

```
<400> SEQUENCE: 1
gcgttactaa ttgatattgg gtttacaata agtatcaatt tgctaaagct agctacaaca      60
gcactacagc agttgtagta ttagttgtta catgattcgt cggactttgt gactctgttt     120
ttctttgctg tttcttgctt tgtgcttgct attacaaggg ttatcttgtg caattagagt     180 tttgggggatt ggatcggatg attatcggat tcaactgcag                           220

<210> SEQ ID NO 2
<211> LENGTH: 136
<212> TYPE: DNA
<213> ORGANISM: Fragaria x ananassa

<400> SEQUENCE: 2
gcttttttag cttttggtat cagaacaata gttcaggcat gtcaacagga aaatgaagta      60
aaccaatgga aagggcaga agaaatgaga ctagaagagg caaaagtagc cgaagaagtt     120
gcaatggaag ctgcag                                                     136

<210> SEQ ID NO 3
<211> LENGTH: 190
<212> TYPE: DNA
<213> ORGANISM: Fragaria x ananassa

<400> SEQUENCE: 3
aacaaatata gtgtaattaa gctactcata gtaggtcgat tggaagaggt gatccagagt      60
tctaaactat atagcatcac tgttcattta aatcgtcacg cagcgcacag taggcttcat     120
tgtgtgagcc aaattgagag tggttggttt tgccaatgtt ttgagcacgt ctgctgcatg     180
taaactgcag                                                            190

<210> SEQ ID NO 4
<211> LENGTH: 508
<212> TYPE: DNA
<213> ORGANISM: Fragaria x ananassa

<400> SEQUENCE: 4
ctgcagaata agttcaacat tatcaaggaa aatgaagcaa tttatctctg caaggtttta      60
gaggtaacaa atttgtagag atctgtggag catgaagaac ttcttaaagt tgcaagtgaa     120
tgaagtggtg caaaggatgt atagcgctat caaccattgc tgaatgtaat cttctcctcg     180
agttcaaaag gaatagcaag tggcaaatta ctaatattgg ccatatggtc tgtaacccaa     240
acatcttcat cagaaattgc atgatgagag gaacgcctct tgagtacttt ctgaagtttg     300
agtagtcatt gcagtaaggg cacatttact aacttggaat gaaaaatatc atgaatcggt     360
atcaacaaga attggtatga gaatatttca ttccattcta ccaaattttt atccaacaca     420
agagtttccg tcatagtgta accagcagag gtgttgttgg ggtctcctga gtcctgactg     480
ctgttaatag ttatcaattt atcataat                                        508

<210> SEQ ID NO 5
<211> LENGTH: 117
<212> TYPE: DNA
<213> ORGANISM: Fragaria x ananassa

<400> SEQUENCE: 5
gacggtattc taatctataa ttaaagagct cagtgatttc attgttgtct aaatagctga      60
atgagtaatt gaggctatgg gccaatgagc ccagcaattt gcacgtactt gctgcag         117
```

```
<210> SEQ ID NO 6
<211> LENGTH: 114
<212> TYPE: DNA
<213> ORGANISM: Fragaria x ananassa

<400> SEQUENCE: 6
tctaaacatg acaagctatc tttcatttta aacagaagtt ttcattttc ttatacgcc      60 taagctaaaa acttttataa tctcatcact aactactagc tactactact gcag         114

<210> SEQ ID NO 7
<211> LENGTH: 281
<212> TYPE: DNA
<213> ORGANISM: Fragaria x ananassa

<400> SEQUENCE: 7
ctgcagaaaa gggagaagaa gttcttggaa agttttgtga tcaaatatca agagcaagta   60
ccgaattatt gagcatattt aaaggtaaaa cgggtctggc ggaactgggc ttaggatttg  120
tgaaaagata tgaagtgaaa caacagtgtg atgattagaa gggtcgtaga accatttcat  180
gtttttgagt gctgttgtca gtctcattaa tacaactgta tatagtgatg actggtgcta  240
atcttctatt tcatctggca ttacaatctt ctattatgag t                      281

<210> SEQ ID NO 8
<211> LENGTH: 112
<212> TYPE: DNA
<213> ORGANISM: Fragaria x ananassa

<400> SEQUENCE: 8
acggttaacc cctcctagaa aatccatatc aatttatata tgtatgtatc tgtatctgta   60
tctatctctc atatctctat gtaactatat aaagacaacc tcacagctgc ag          112

<210> SEQ ID NO 9
<211> LENGTH: 123
<212> TYPE: DNA
<213> ORGANISM: Fragaria x ananassa

<400> SEQUENCE: 9
atcttcaata gccgaccagt cgctatgttt ttattttgtt caaattgtac gtgtgtgtcc   60
tcaatagttt cttttcaaat atgaaggatg gtgccgctgt agctggtctt gctattgctg  120
cag                                                                123

<210> SEQ ID NO 10
<211> LENGTH: 301
<212> TYPE: DNA
<213> ORGANISM: Fragaria x ananassa

<400> SEQUENCE: 10
ctgcagcgga ggcgcctgcc gactccaacc ctgatgttga gattgataaa aatatgggga   60
ataatatggt catagttgga cactgaccga gccagccatg ggcctagtgc tagctgatgc  120
ttttatatag ggaaaattgt ccaaacagtg tctcaccttt tagaaaaact aacttttggt  180
atctcaactt ttaaaaactt caaaacggta tctcacgttt ctacttcaac cgaaatatgg  240
tacctgcaac tgttaatttt gttaaaacaa ctgacagatt aagggtattt tcgtcctttc  300
a                                                                  301
```

```
<210> SEQ ID NO 11
<211> LENGTH: 18
<212> TYPE: DNA
<213> ORGANISM: Artificial Sequence
<220> FEATURE:
<223> OTHER INFORMATION: Synthetic DNA

<400> SEQUENCE: 11
cacgatggat ccagtgca                                                   18

<210> SEQ ID NO 12
<211> LENGTH: 16
<212> TYPE: DNA
<213> ORGANISM: Artificial Sequence
<220> FEATURE:
<223> OTHER INFORMATION: Synthetic DNA

<400> SEQUENCE: 12
ctggatccat cgtgca                                                     16

<210> SEQ ID NO 13
<211> LENGTH: 16
<212> TYPE: DNA
<213> ORGANISM: Artificial Sequence
<220> FEATURE:
<223> OTHER INFORMATION: Synthetic DNA

<400> SEQUENCE: 13
gatggatcca gtgcag                                                     16

<210> SEQ ID NO 14
<211> LENGTH: 71
<212> TYPE: DNA
<213> ORGANISM: Artificial Sequence
<220> FEATURE:
<223> OTHER INFORMATION: Synthetic DNA

<400> SEQUENCE: 14
gcgttactaa ttgatattgg gtttacaata agtatcaatt tgctaaagct agctacaaca     60
gcactacagc a                                                          71

<210> SEQ ID NO 15
<211> LENGTH: 57
<212> TYPE: DNA
<213> ORGANISM: Artificial Sequence
<220> FEATURE:
<223> OTHER INFORMATION: Synthetic DNA

<400> SEQUENCE: 15
tgaagtaaac caatggaaaa gggcagaaga aatgagacta gaagaggcaa aagtagc        57

<210> SEQ ID NO 16
<211> LENGTH: 60
<212> TYPE: DNA
<213> ORGANISM: Artificial Sequence
<220> FEATURE:
<223> OTHER INFORMATION: Synthetic DNA

<400> SEQUENCE: 16
tggaagaggt gatccagagt tctaaactat atagcatcac tgttcattta aatcgtcacg     60

<210> SEQ ID NO 17
<211> LENGTH: 68
<212> TYPE: DNA
<213> ORGANISM: Artificial Sequence
```

```
<220> FEATURE:
<223> OTHER INFORMATION: Synthetic DNA

<400> SEQUENCE: 17
gaataagttc aacattatca aggaaaatga agcaatttat ctctgcaagg ttttagaggt    60
aacaaatt                                                              68

<210> SEQ ID NO 18
<211> LENGTH: 53
<212> TYPE: DNA
<213> ORGANISM: Artificial Sequence
<220> FEATURE:
<223> OTHER INFORMATION: Synthetic DNA

<400> SEQUENCE: 18
attgttgtct aaatagctga atgagtaatt gaggctatgg gccaatgagc cca            53

<210> SEQ ID NO 19
<211> LENGTH: 62
<212> TYPE: DNA
<213> ORGANISM: Artificial Sequence
<220> FEATURE:
<223> OTHER INFORMATION: Synthetic DNA

<400> SEQUENCE: 19
tttcatttta aacagaagtt ttcattttc tttatacgcc taagctaaaa acttttataa     60
tc                                                                    62

<210> SEQ ID NO 20
<211> LENGTH: 69
<212> TYPE: DNA
<213> ORGANISM: Artificial Sequence
<220> FEATURE:
<223> OTHER INFORMATION: Synthetic DNA

<400> SEQUENCE: 20
gtgctgttgt cagtctcatt aatacaactg tatatagtga tgactggtgc taatcttcta    60
tttcatctg                                                             69

<210> SEQ ID NO 21
<211> LENGTH: 73
<212> TYPE: DNA
<213> ORGANISM: Artificial Sequence
<220> FEATURE:
<223> OTHER INFORMATION: Synthetic DNA

<400> SEQUENCE: 21
tgtatgtatc tgtatctgta tctatctctc atatctctat gtaactatat aaagacaacc    60
tcacagctgc act                                                        73

<210> SEQ ID NO 22
<211> LENGTH: 68
<212> TYPE: DNA
<213> ORGANISM: Artificial Sequence
<220> FEATURE:
<223> OTHER INFORMATION: Synthetic DNA

<400> SEQUENCE: 22
gccgaccagt cgctatgttt ttattttgtt caaattgtac gtgtgtgtcc tcaatagttt    60
cttttcaa                                                              68
```

```
<210> SEQ ID NO 23
<211> LENGTH: 66
<212> TYPE: DNA
<213> ORGANISM: Artificial Sequence
<220> FEATURE:
<223> OTHER INFORMATION: Synthetic DNA

<400> SEQUENCE: 23
cgtttctact tcaaccgaaa tatggtacct gcaactgtta attttgttaa aacaactgac    60
agatta                                                              66

<210> SEQ ID NO 24
<211> LENGTH: 23
<212> TYPE: DNA
<213> ORGANISM: Artificial Sequence
<220> FEATURE:
<223> OTHER INFORMATION: Synthetic DNA

<400> SEQUENCE: 24
cggttaaccc ctcctagaaa atc                                           23

<210> SEQ ID NO 25
<211> LENGTH: 23
<212> TYPE: DNA
<213> ORGANISM: Artificial Sequence
<220> FEATURE:
<223> OTHER INFORMATION: Synthetic DNA

<400> SEQUENCE: 25
tgcagctgtg aggttgtctt tat                                           23

<210> SEQ ID NO 26
<211> LENGTH: 24
<212> TYPE: DNA
<213> ORGANISM: Artificial Sequence
<220> FEATURE:
<223> OTHER INFORMATION: Synthetic DNA

<400> SEQUENCE: 26
ctgcagaaaa gggagaagaa gttc                                          24

<210> SEQ ID NO 27
<211> LENGTH: 26
<212> TYPE: DNA
<213> ORGANISM: Artificial Sequence
<220> FEATURE:
<223> OTHER INFORMATION: Synthetic DNA

<400> SEQUENCE: 27
gccagatgaa atagaagatt agcacc                                        26

<210> SEQ ID NO 28
<211> LENGTH: 26
<212> TYPE: DNA
<213> ORGANISM: Artificial Sequence
<220> FEATURE:
<223> OTHER INFORMATION: Synthetic DNA

<400> SEQUENCE: 28
gctactcata gtaggtcgat tggaag                                        26

<210> SEQ ID NO 29
<211> LENGTH: 21
<212> TYPE: DNA
<213> ORGANISM: Artificial Sequence
```

```
<220> FEATURE:
<223> OTHER INFORMATION: Synthetic DNA

<400> SEQUENCE: 29
ctgcagttta catgcagcag a                                              21

<210> SEQ ID NO 30
<211> LENGTH: 27
<212> TYPE: DNA
<213> ORGANISM: Artificial Sequence
<220> FEATURE:
<223> OTHER INFORMATION: Synthetic DNA

<400> SEQUENCE: 30
aagttcaaca ttatcaagga aaatgaa                                        27

<210> SEQ ID NO 31
<211> LENGTH: 27
<212> TYPE: DNA
<213> ORGANISM: Artificial Sequence
<220> FEATURE:
<223> OTHER INFORMATION: Synthetic DNA

<400> SEQUENCE: 31
aattgataac tattaacagc agtcagg                                        27

<210> SEQ ID NO 32
<211> LENGTH: 508
<212> TYPE: DNA
<213> ORGANISM: Fragaria x ananassa

<400> SEQUENCE: 32
ctgcagaata agttcaacat tatcaaggaa aatgaagcaa tttatctctg caaggtttta    60
gaggtaacaa atttgtagag atctgtggag catgaagaac ttcttaaagt tgcaagtgaa   120
tgaagtggtg caaaggatgt atagcgctat caaccattgc tgaatgtaat cttctcctcg   180
agttcaaaag gaatagcaag tggcaaatta ctaatattgg ccatatggtc tgtaacccaa   240
acatcttcat cagaaaatgc atgatgagag gaacgcctct tgagtacttt ctgaagtttg   300
agtagtcatt gcagtaaggg cacatttact aacttggaat gaaaaatatc atgaatcggt   360
atcaacaaga attggtatga gaatatttca ttccattcta ccaaattttt atccaacaca   420
agagtttccg tcatagtgta accagcagag gtgttgttgg ggtctcctga gtcctgactg   480
ctgttaatag ttatcaattt atcataat                                     508
```

MARKER ASSOCIATED WITH ANTHRACNOSE RESISTANCE IN PLANT OF THE GENUS *FRAGARIA* AND USE THEREOF

This application is a National Stage of International Application No. PCT/JP2014/073460 filed Sep. 5, 2014, claiming priority based on Japanese Patent Application Nos. 2013-186688 filed Sep. 9, 2013 and 2014-165405 dated Aug. 15, 2014, the contents of all of which are incorporated herein by reference in their entirety.

TECHNICAL FIELD

The present invention relates to a marker associated with anthracnose resistance that enables selection of a plant line of the genus *Fragaria* exhibiting resistance against strawberry anthracnose and use thereof.

BACKGROUND ART

With the development of DNA markers (also referred to as genetic markers or gene markers), both useful and undesirable traits can be rapidly and efficiently identified when improvement in plant varieties is intended. The development of DNA markers has advanced for a wide variety of practical plants as well as for model plants such as *Arabidopsis thaliana* and *Oryza sativa*. Thus, such markers significantly contribute to improvement in plant varieties.

DNA Research 20, 79-92, 2013 reports the development of integrated high-density linkage maps of strawberry cultivars. According to DNA Research 20, 79-92, 2013, linkage maps comprising approximately 300 amplified fragment length polymorphism (AFLP) markers have heretofore been reported; however, the development of higher-density linkage maps of strawberry cultivars has been desired because of the complex genomic structures thereof; that is, they are octaploids. According to DNA Research 20, 79-92, 2013, also, simple sequence repeat markers were developed for *F. vessca* and *F. x ananassa*, and integrated high-density linkage maps thereof were constructed. More specifically, linkage maps were prepared using 5 plant varieties; i.e., 02-19, Sachinoka, Kaorino, Akihime, and 0212921, and these maps were integrated so as to construct an integrated high-density linkage map. According to DNA Research 20, 79-92, 2013, the number of markers developed for the 02-19 cultivar is 575, that for the Sachinoka cultivar is 556, that for the Kaorino cultivar is 294, that for the Akihime cultivar is 318, and that for the 0212921 cultivar is 822. In the integrated high-density linkage map disclosed in DNA Research 20, 79-92, 2013, however, there are linkage groups without markers to be located, and such phenomenon is more apparent in the Kaorino and Akihime cultivars, to which small numbers of markers are developed. In addition, the integrated high-density linkage map disclosed in DNA Research 20, 79-92, 2013 is not considered to encompass all linkage maps.

Also, Tochigi Prefectural Agricultural Experiment Station, Abstracts of Research Results, No. 29, pp. 51-52 describes that DNA markers linked to strawberry anthracnose resistance were developed so as to efficiently develop strawberry anthracnose-resistant varieties. According to Tochigi Prefectural Agricultural Experiment Station, Abstracts of Research Results, No. 29, pp. 51-52, linkage maps were prepared using markers by the Random Amplified Polymorphic DNA (RAPD) method, the AFLP method, and the SSR method, and markers associated with anthracnose resistance were analyzed. This resulted in the development of markers that could reduce the breeding population to one-eighth with the use thereof for the population crossed with the Strawberry Parental Line Nou-2 and could be used to identify the anthracnose-resistant varieties with a probability of about 70% according to Tochigi Prefectural Agricultural Experiment Station, Abstracts of Research Results, No. 29, pp. 51-52.

As described in Microbiol. Cult. Coll., 25(1): 27-32, 2009, *Glomerella cingulata* and *Colletotrichum acutatum* are known to cause strawberry anthracnose.

Meanwhile, WO 2007/125958 discloses the development of markers for selection of sugar beet black rot resistant varieties and JP 2010-516236 A discloses a technique for selection involving the use of markers linked to the target traits in maize.

SUMMARY OF THE INVENTION

Objects to be Attained by the Invention

To date, DNA marker technologies that had been developed in plants such as sugar beet or maize as described above have not been substantially advanced in plants of the genus *Fragaria*. While DNA Research 20, 79-92, 2013 describes that SSR markers were developed and the integrated high-density linkage maps thereof were constructed, such techniques were not sufficient for selection of DNA markers linked to the target traits of plants of the genus *Fragaria*, which are polyploids with complex genomic structures. In addition, Tochigi Prefectural Agricultural Experiment Station, Abstracts of Research Results, No. 29, pp. 51-52 describes the development of DNA markers linked to strawberry anthracnose resistance. However, the logarithm of odds (LOD) and the contribution ratio thereof were not found to be sufficient as a result of QTL analysis, and such markers could not be evaluated as excellent markers.

Under the above circumstances, it is an object of the present invention to develop many DNA markers in plants of the genus *Fragaria*, which are polyploids with complex genomic structures. It is another object to provide markers associated with anthracnose resistance that enable evaluation of anthracnose resistance with high accuracy with the use of such many DNA markers and a method of using such markers.

Means for Attaining the Objects

The present inventors have conducted concentrated studies in order to attain the above objects. As a result, they discovered markers linked to quantitative traits, such as anthracnose resistance, by preparing many markers in plants of the genus *Fragaria* and conducting linkage analysis between quantitative traits and markers in hybrid progeny lines. This has led to the completion of the present invention.

The present invention includes the following.

(1) A marker associated with anthracnose resistance in plants of the genus *Fragaria* comprising a continuous nucleic acid region sandwiched between the nucleotide sequence as shown in SEQ ID NO: 1 and the nucleotide sequence as shown in SEQ ID NO: 10 in the chromosome of the plant of the genus *Fragaria*.

(2) The marker associated with anthracnose resistance in plants of the genus *Fragaria* according to (1), wherein the nucleic acid region comprises any nucleotide sequence selected from the group consisting of nucleotide sequences as shown in SEQ ID NOs: 1 to 10 or a part of the nucleotide sequence.

(3) The marker associated with anthracnose resistance in plants of the genus *Fragaria* according to (1), wherein the nucleic acid region is located in a region sandwiched between the nucleotide sequence as shown in SEQ ID NO: 4 and the nucleotide sequence as shown in SEQ ID NO: 8 in the chromosome of the plant of the genus *Fragaria*.

(4) A method for producing a plant line of the genus *Fragaria* with improved anthracnose resistance comprising:
a step of extracting a chromosome of a progeny plant whose at least one parent is a plant of the genus *Fragaria* and/or a chromosome of the parent plant of the genus *Fragaria*; and
a step of determining the presence or absence of the marker associated with anthracnose resistance in the plant of the genus *Fragaria* according to any one of (1) to (3) above in the chromosome obtained above.

(5) The method for producing a plant line of the genus *Fragaria* according to (4), wherein the step of determination comprises conducting a nucleic acid amplification reaction using a primer that specifically amplifies the marker associated with anthracnose resistance in the plant of the genus *Fragaria* to determine the presence or absence of the marker associated with anthracnose resistance in the plant of the genus *Fragaria*.

(6) The method for producing a plant line of the genus *Fragaria* according to (4), wherein the step of determination involves the use of a DNA chip comprising a probe corresponding to the marker associated with anthracnose resistance in the plant of the genus *Fragaria*.

(7) The method for producing a plant line of the genus *Fragaria* according to (4), wherein the progeny plant is a seed or seedling and the chromosome is extracted from the seed or seedling.

This description includes part or all of the content as disclosed in the descriptions and/or drawings of Japanese Patent Application Nos. 2013-186688 and 2014-165405, which are priority documents of the present application.

Effects of the Invention

The present invention provides novel markers associated with anthracnose resistance in plants of the genus *Fragaria* that are linked to anthracnose resistance among various quantitative traits of plants of the genus *Fragaria*. With the use of the markers associated with anthracnose resistance in plants of the genus *Fragaria* according to the present invention, anthracnose resistance in hybrid lines of the plants of the genus *Fragaria* can be tested. Thus, plant lines of the genus *Fragaria* with improved anthracnose resistance can be identified in a very cost-effective manner.

BRIEF DESCRIPTION OF THE DRAWINGS

FIG. 22 is a table showing a summary of the results of detection of signals of markers from the IA204069 marker to the IA201502 marker concerning Sachinoka, Strawberry Parental Line Nou-2, and progeny lines thereof with the use of the probes shown in Table 3.

EMBODIMENTS FOR CARRYING OUT THE INVENTION

Figure 1:
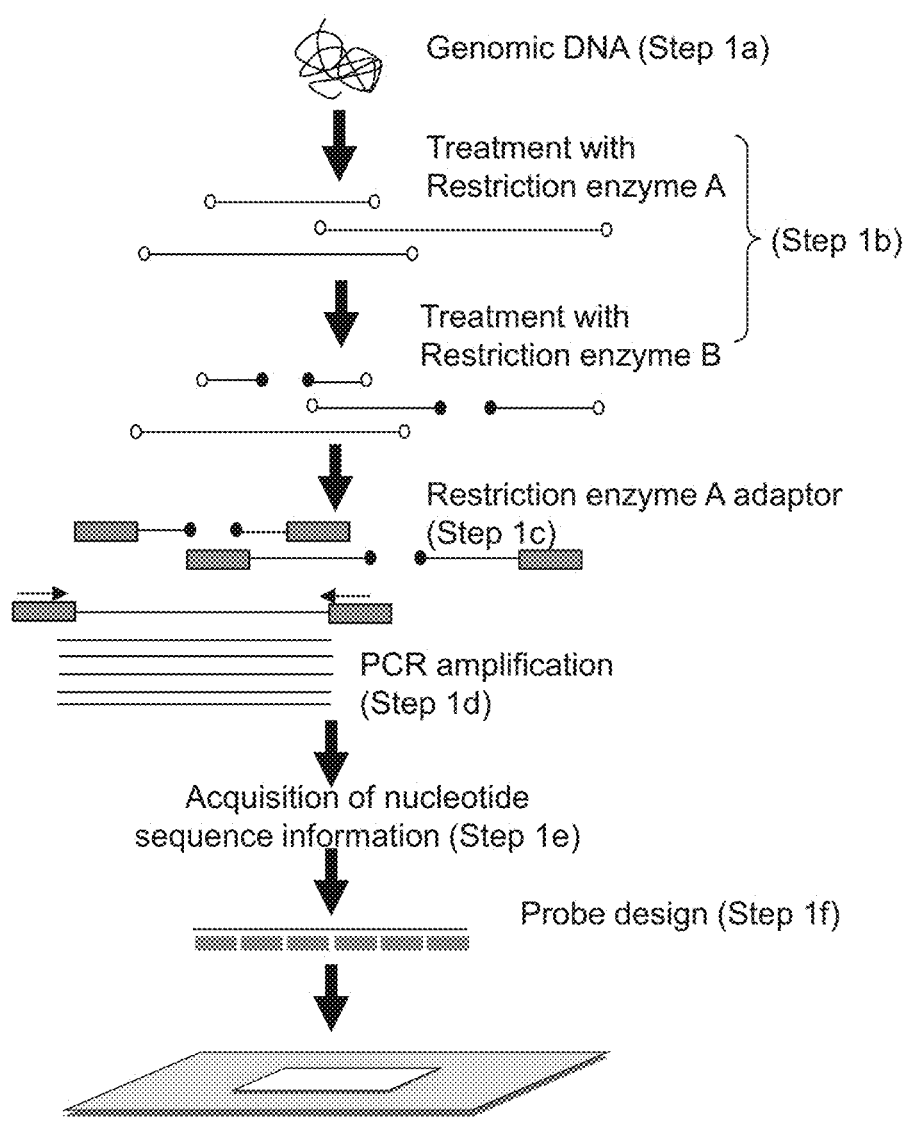
FIG. 1 schematically shows a process for producing a DNA microarray used for obtaining markers in chromosomes of plants of the genus *Fragaria*.

Hereafter, the markers associated with anthracnose resistance in a plant of the genus *Fragaria* of the present invention, the method for using the same, and, in particular, a method for producing plant lines of the genus *Fragaria* using the markers associated with anthracnose resistance in plants of the genus *Fragaria* are described.

[Markers Associated with Anthracnose Resistance in Plants of the Genus *Fragaria*]

The marker associated with anthracnose resistance in a plant of the genus *Fragaria* according to the present invention is a particular region in the chromosome of a plant of the genus *Fragaria* that makes it possible to identify traits of anthracnose resistance of a plant of the genus *Fragaria*. By determining the presence or absence of the marker associated with anthracnose resistance in the plant of the genus *Fragaria* in the progeny lines obtained from existing plants of the genus *Fragaria*, specifically, whether or not a line of interest has traits of improved anthracnose resistance can be determined. In the present invention, the term "strawberry anthracnose" refers to a disease resulting from infection with *Glomerella cingulata* and/or *Colletotrichum acutatum*, leading to development of lesions, as described in Microbiol. Cult. Coll., 25(1): 27-32, 2009. In particular, the term "strawberry anthracnose" used herein may be identified as a disease caused by infection with *Glomerella cingulata*.

The markers associated with anthracnose resistance in plants of the genus *Fragaria* refers to both a marker linked to improved anthracnose resistance and a marker linked to reduced anthracnose resistance. When the former marker is present in a given plant of the genus *Fragaria*, for example, it can be determined that such plant variety has improved anthracnose resistance. When the former marker is present and the latter marker is absent in a given plant of the genus *Fragaria*, in addition, it can be determined that such plant variety has improved anthracnose resistance with higher accuracy. It can be determined that a plant variety has improved anthracnose resistance based only on the absence of the latter marker in a given plant of the genus *Fragaria*.

In particular, the former marker associated with anthracnose resistance in plants of the genus *Fragaria* can be considered to be a region linked to a causative gene (or genes) for traits of a plant of the genus *Fragaria* such as anthracnose resistance.

The term "plants of the genus *Fragaria*" used herein refers to all plants belonging to the rosaceous genus *Fragaria* (*Fragaria* L.). Specific examples of plants of the genus *Fragaria* include hybrids of general strawberry cultivars, *Fragaria ananassa* (i.e., *Fragaria* x *ananassa*). Examples of plants of the genus *Fragaria* include plants of *F. virginiana* that are progenitor species of strawberry cultivars and plants of wild species, such as *F. chiloensis, F. vesca, F. iinumae, F. nipponica, F. nubicola, F. bucharica, F. daltoniana, F. orientalis, F. corimbosa, F. moschata*, and *F. iturupensis*. Further, "plants of the genus *Fragaria*" encompass known varieties and lines of strawberry cultivars (*F.* x *ananassa*). Known varieties and lines of strawberry cultivars are not particularly limited, and any varieties and lines that can be used inside or outside Japan are within the scope thereof. For example, strawberry cultivars grown in Japan are not particularly limited. Examples thereof include Toyonoka, Sanchigo, June berry, Nyoho, Pisutoro, Rindamore, Tochiotome, Aisutoro, Tochinomine, Akihime, Benihoppe, Tochihime, Sachinoka, Keikiwase, Sagahonoka, Aiberry, Karen berry, Red pearl, Satsumaotome, Fukuoka S6 (Amaou), Nohime, Hinomine, and Houkou-wase. Examples of strawberry cultivars include Strawberry Parental Line Nou-1 and Strawberry Parental Line Nou-2 that are parental lines used for plant variety improvement aimed at acquisition of particular properties. Strawberry Parental Line Nou-2 results from hybridization of 83118-41 with improved anthracnose resistance and a resistant variety, Dover. The level of anthracnose resistance of the Strawberry Parental Line Nou-2 is equivalent to or higher than that of the resistant variety Houkou-wase or Dover. In the group of seedlings resulting from crossing between a resistant variety and a susceptible variety, also, highly resistant plants are likely to develop. Thus, such lines are used for breeding new varieties with strawberry anthracnose resistance.

The presence or absence of the marker associated with anthracnose resistance in a plant of the genus *Fragaria* can be determined in the above plants of the genus *Fragaria* and progeny lines of the above plants of the genus *Fragaria*. In a progeny line, either the mother plant or father plant may be a plant of the genus *Fragaria* described above. A progeny line may result from sibling cross or may be a hybrid line. Alternatively, a progeny line may result from so-called backcrossing.

It is particularly preferable that the presence or absence of the marker associated with anthracnose resistance in the plant of the genus *Fragaria* be determined in strawberry cultivars (*F.* x *ananassa*). In addition, it is preferable that the presence or absence of the marker associated with anthracnose resistance in the plant of the genus *Fragaria* be determined in improved lines resulting from various varieties and lines of the strawberry cultivars described above. In such a case, strawberry anthracnose resistance can be evaluated in produced new varieties. Accordingly, it is preferable that a new variety be derived from a line having strawberry anthracnose resistance as either the mother plant or father plant. More specifically, for example, the presence or absence of the marker associated with anthracnose resistance in a plant of the genus *Fragaria* in a new variety produced from the Strawberry Parental Line Nou-2 as a parent may be determined, so as to evaluate its resistance to strawberry anthracnose.

The marker associated with anthracnose resistance in plants of the genus *Fragaria* according to the present invention has been newly identified by QTL (Quantitative Trait Loci) analysis using a genetic linkage map containing 1,502 markers acquired from the strawberry cultivar Sachinoka and 2,162 markers acquired from the Strawberry Parental Line Nou-2 and data concerning strawberry anthracnose resistance. Many genes are considered to be associated with strawberry anthracnose resistance, which is a quantitative trait exhibiting a continuous distribution. Specifically, strawberry anthracnose resistance is evaluated based on rates of affection with strawberry anthracnose, which exhibits a continuous distribution. QTL analysis is carried out with the use of the gene analysis software of QTL Cartographer (Wang S., C. J. Basten and Z.-B. Zeng, 2010, Windows QTL Cartographer 2.5. Department of Statistics, North Carolina State University, Raleigh, N.C.) in accordance with the composite interval mapping (CIM) method.

Specifically, a region exhibiting a LOD score equivalent to or higher than a given threshold (e.g., 2.5) was found in the gene linkage maps by the QTL analysis. The size of this region is approximately 29.0 cM (centimorgan), and this region is included in the 23rd linkage group of Strawberry Parental Line Nou-2. The unit "morgan (M)" relatively indicates a distance between genes on the chromosome, and such distance is represented in terms of a percentage of the crossing-over value. In the chromosome of a plant of the genus *Fragaria*, "1 cM" is equivalent to approximately 400 kb. This region has a peak whose LOD score is approximately 18.3. This implies the presence of causal gene(s) that improve anthracnose resistance in plants of the genus *Fragaria* at such peak or in the vicinity thereof.

The 29.0-cM region comprises the 10 types of markers shown in Table 1 in the order shown in Table 1. The marker names indicated in Table 1 were acquired exclusively for the present invention.

TABLE 1

| SEQ ID NO | Marker Name | Nucleotide sequence Information |
|---|---|---|
| 1 | IA204069 | GCGTTACTAATTGATATTGGGTTTACAATAAGTATCAATTTGCTAAAGCTAGCTACAACAGCACTACAGCAGTT GTAGTATTAGTTGTTACATGATTCGTCGGACTTTGTGACTCTGTTTTTCMGCTUTTCTTGCTTTGTGCTTG CTATTACAAGGGTTATCTTGTGCAATTAGAGTTTTGGGGATTGGATCGGATGATTATCGGATTCAACTGCAG |
| 2 | IA204291 | GCTTTTTTAGCTTTTGGTATCAGAACAATAGTTCAGGCATGTCAACAGGAAAATGAAGTAAACCAATGGAAAAG GGCAGAAGAAATGAGACTAGAAGAGGCAAAAGTAGCCGAAGAAGTTGCAATGGAAGCTGCAG |
| 3 | IA202531 | AACAAATATAGTGTAATTAAGCTACTCATAGTAGGTCGATTGGAAGAGGTGATCCAGAGTTCTAAACTATATAG CATCACTGTTCATTTAAATCGTCACGCAGCGCACAGTAGGCTTCATTGTGTGAGCCAAATTGAGAGTGGTTGGT TTTGCCAATGTTTTGAGCACGTCTGCTGCATGTAAACTGCAG |
| 4 | IA200064 | CTGCAGAATAAGTTCAACATTATCAAGGAAAATGAAGCAATTTATCTCTGCAAGGTTTTAGAGGTAACAAATTT GTAGAGATCTGTGGAGCATGAAGAACTTCTTAAAGTTGCAAGTGAATGAAGTGGTGCAAAGGATGTATAGCGCT ATCAACCATTGCTGAATGTAATCTTCTCCTCGAGTTCAAAAGGAATAGCAAGTGGCAAATTACTAATATTGGCC ATATGGTCTGTAACCCAAACATCTTCATCAGAAATTGCATGATGAGAGGAACGCCTCTTGAGTACTTTCTGAAG TTTGAGTAGTCATTGCAGTAAGGGCACATTTACTAACTTGGAATGAAAAATATCATGAATCGGTATCAACAAGA ATTGGTATGAGAATATTTCATTCCATTCTACCAAATTTTTATCCAACACAAGAGMCCGTCATAGTGTAACCA GCAGAGGTGTTGTTGGGGTCTCCTGAGTCCTGACTGCTGTTAATAGTTATCAATTTATCATAAT |
| 5 | IA205184 | GACGGTATTCTAATCTATAATTAAAGAGCTCAGTGATTTCATTGTTGTCTAAATAGCTGAATGAGTAATTGAGG CTATGGGCCAATGAGCCCAGCAATTTGCACGTACTTGCTGCAG |
| 6 | IA202854 | TCTAAACATGACAAGCTATCTTTCATTTTAAACAGAAGTTTTCATTTTTCTTTATACGCCTAAGCTAAAAACTT TTATAATCTCATCACTAACTACTAGCTACTACTACTGCAG |
| 7 | IA200826 | CTGCAGAAAAGGGAGAAGAAGTTCTTGGAAAGTTTTGTGATCAAATATCAAGAGCAAGTACCGAATTATTGAGC ATATTTAAAGGTAAAACGGGTCTGGCGGAACTGGGCTTAGGATTTGTGAAAAGATATGAAGTGAAACAACAGTG TGATGATTAGAAGGGTCGTAGAACCATTTCATGTTTTTGAGTGCTGTTGTCAGTCTCATTAATACAACTGTATA TAGTGATGACTGGTGCTAATCTTCTATTTCATCTGGCATTACAATCTTCTATTATGAGT |
| 8 | IA202631 | ACGGTTAACCCCTCCTAGAAAATCCATATCAATTTATATATGTATGTATCTGTATCTGTATCTATCTCTCATAT CTCTATGTAACTATATAAAGACAACCTCACAGCTGCAG |
| 9 | IA202517R | ATCTTCAATAGCCGACCAGTCGCTATGTTTTTATTTTGTTCAAATTGTACGTGTGTGTCCTCAATAGTTTCTTT TCAAATATGAAGGATGGTGCCGCTGTAGCTGGTCTTGCTATTGCTGCAG |
| 10 | IA201502 | CTGCAGCGGAGGCGCCTGCCGACTCCAACCCTGATGTTGAGATTGATAAAAATATGGGGAATAATATGGTCATA GTTGGACACTGACCGAGCCAGCCATGGGCCTAGTGCTAGCTGATGCTTTTATATAGGGAAAATTGTCCAAACAG TGTCTCACCTTTTAGAAAAACTAACTTTTGGTATCTCAACTTTTAAAAACTTCAAAACGGTATCTCACGTTTCT ACTTCAACCGAAATATGGTACCTGCAACTGTTAATTTTGTTAAAACAACTGACAGATTAAGGGTATTTTCGTCC TTTCA |

Specifically, the marker associated with anthracnose resistance in plants of the genus *Fragaria* according to the present invention is a continuous nucleic acid region sandwiched between the nucleotide sequence as shown in SEQ ID NO: 1 and the nucleotide sequence as shown in SEQ ID NO: 10 in the chromosome of the plant of the genus *Fragaria*. The peak in the 29.0-cM region is located in a region sandwiched between the marker consisting of the nucleotide sequence as shown in SEQ ID NO: 4 (IA200064) and the marker consisting of the nucleotide sequence as shown in SEQ ID NO: 8 (IA202631).

Also, such 29.0-cM region contains a marker linked to traits that improve anthracnose resistance and a marker linked to traits that reduce anthracnose resistance. Among the ten types of markers shown in Table 1, a marker comprising the nucleotide sequence as shown in SEQ ID NO: 9 (IA202517R) is a marker linked to traits that reduce anthracnose resistance (i.e., an opposing marker), and all other markers are linked to traits that improve anthracnose resistance.

A continuous nucleic acid region in the 29.0-cM region shown in Table 1 can be used as the marker associated with anthracnose resistance in plants of the genus *Fragaria*. The term "nucleic acid region" used herein refers to a region comprising a nucleotide sequence having 95% or less, preferably 90% or less, more preferably 80% or less, and most preferably 70% or less identity to the other region in the chromosome of the plant of the genus *Fragaria*. As long as the degree of identity between the nucleic acid region as the marker associated with anthracnose resistance in plants of the genus *Fragaria* and the other region is within the range described above, such nucleic acid region can be specifically detected in accordance with a conventional technique. The degree of identity can be determined using, for example, BLAST with the default parameters.

A nucleic acid region serving as the marker associated with anthracnose resistance in plants of the genus *Fragaria* can comprise at least 8, preferably 15 or more, more preferably 20 or more, and most preferably 30 nucleotides. As long as the number of nucleotides constituting the nucleic acid region as the marker associated with anthracnose resistance in plants of the genus *Fragaria* is within such range, such nucleic acid region can be specifically detected in accordance with a conventional technique.

In particular, the marker associated with anthracnose resistance in plants of the genus *Fragaria* is preferably selected from a region sandwiched between the nucleotide sequence as shown in SEQ ID NO: 4 and the nucleotide sequence as shown in SEQ ID NO: 8 among the ten types of markers included in the 29.0-cM region because the peak is located in the region sandwiched between the nucleotide sequence as shown in SEQ ID NO: 4 and the nucleotide sequence as shown in SEQ ID NO: 8.

The marker associated with anthracnose resistance in plants of the genus *Fragaria* can be a nucleic acid region including a single type of marker selected from among the ten types of markers shown in Table 1. For example, use of a nucleic acid region including a marker consisting of the nucleotide sequence as shown in SEQ ID NO: 8 (IA202631), which is located in a position nearest to the peak as the marker associated with anthracnose resistance in plants of the genus *Fragaria* is preferable. In such a case, the nucleotide sequence of the nucleic acid region including the marker can be identified by a method of franking sequence analysis, such as inverse PCR using primers designed based on the nucleotide sequence of the marker.

Alternatively, a plurality of regions may be selected from a nucleic acid region sandwiched between the nucleotide sequence as shown in SEQ ID NO: 1 and the nucleotide sequence as shown in SEQ ID NO: 10 in the chromosome of the plant of the genus *Fragaria* as the marker associated with anthracnose resistance in the plant of the genus *Fragaria*.

In addition, any of the above ten types of markers can be directly used as markers associated with anthracnose resistance in plants of the genus *Fragaria*. Specifically, one or more regions selected from the ten regions comprising the nucleotide sequences as shown in SEQ ID NOs: 1 to 10 can be used as markers associated with anthracnose resistance in plants of the genus *Fragaria*. For example, use of a marker consisting of the nucleotide sequence as shown in SEQ ID NO: 8 (IA202631), which is located in a position nearest to the peak, as a marker associated with anthracnose resistance in plants of the genus *Fragaria* is preferable. Alternatively, a region sandwiched between the marker consisting of the nucleotide sequence as shown in SEQ ID NO: 7 (IA200826) and the marker consisting of the nucleotide sequence as shown in SEQ ID NO: 8 (IA202631) can be used as a marker associated with anthracnose resistance in plants of the genus *Fragaria*, for example.

[Identification of a Marker in Plants of the Genus *Fragaria*]

In the present invention, as described above, the markers associated with anthracnose resistance in plants of the genus *Fragaria* were identified from among the 1,502 markers acquired from Sachinoka and the 2,162 markers acquired from Strawberry Parental Line Nou-2. Such 1,502 markers and 2,162 markers are described below. These markers can be identified with the use of a DNA microarray in accordance with the methods disclosed in JP 2011-120558 A or WO 2011/074510.

Specifically, probes used for the DNA microarray are designed in the manner shown in FIG. 1. That is, genomic DNA is first extracted from Sachinoka or Strawberry Parental Line Nou-2 (Step 1a). Subsequently, the extracted genomic DNA is digested with one or more restriction enzymes (Step 1b). In an embodiment shown in FIG. 1, two types of restriction enzyme, Restriction enzyme A and Restriction enzyme B, are used in that order to digest genomic DNA. Restriction enzymes are not particularly limited, and examples of restriction enzymes that can be used include PstI, EcoRI, HindIII, BstNI, HpaII, and HaeIII. Restriction enzymes can be adequately selected by taking, for example, the frequency of appearance of recognition sequence into consideration, so as to yield a genomic DNA fragment with 20 to 10,000 nucleotides upon complete digestion of genomic DNA. When a plurality of restriction enzymes are used, it is preferable that the genomic DNA fragment comprise 200 to 6,000 nucleotides after all the restriction enzymes are used. When a plurality of restriction enzymes are used, in addition, the order in which restriction enzymes are subjected to treatment is not particularly limited. Under common treatment conditions (e.g., a solution composition or temperature), a plurality of restriction enzymes may be used in the same reaction system. While Restriction enzyme A and Restriction enzyme B are successively used in that order so as to digest genomic DNA in an embodiment shown in FIG. 1, specifically, Restriction enzyme A and Restriction enzyme B may be simultaneously used in the same reaction system to digest genomic DNA. Alternatively, Restriction enzyme B and Restriction enzyme A may be successively used in that order, so as to digest genomic DNA. In addition, 3 or more restriction enzymes may be used.

Subsequently, adaptors are bound to the genomic DNA fragment treated with restriction enzymes (Step 1c). The adaptors used herein are not particularly limited, provided that such adaptors can be bound to the both ends of the genomic DNA fragment obtained through the treatment with restriction enzymes. An example of an adaptor that can be used is an adaptor comprising a single strand that is complementary to a protruding end (a sticky end) formed at both ends of the genomic DNA fragment obtained through the treatment with a restriction enzyme and having a primer-binding sequence to which a primer used at the time of amplification can hybridize (details are described below). Alternatively, an adaptor comprising a single strand complementary to a protruding end (a sticky end) and having a restriction enzyme recognition site to be incorporated into a vector at the time of cloning can be used.

When genomic DNA is digested with a plurality of restriction enzymes, a plurality of adaptors corresponding to relevant restriction enzymes can be used. Specifically, a plurality of adaptors each comprising a single strand complementary to any of a plurality of types of protruding ends resulting from digestion of genomic DNA with a plurality of types of restriction enzymes can be used. In such a case, a plurality of adaptors corresponding to a plurality of restriction enzymes may have common primer-binding sequences enabling hybridization of common primers. Alternatively, such adaptors may have different primer-binding sequences, so that different primers can bind thereto.

When genomic DNA is digested with a plurality of restriction enzymes, in addition, an adaptor corresponding to a restriction enzyme selected from among the plurality of restriction enzymes used or adaptors corresponding to a subset of restriction enzymes selected from among the plurality of restriction enzymes used can be prepared.

Subsequently, a genomic DNA fragment comprising adaptors bound to both ends thereof is amplified (Step 1d). When adaptors comprising primer-binding sequences are used, primers that can hybridize to such primer-binding sequences may be used, so that the genomic DNA fragment can be amplified. Alternatively, a genomic DNA fragment comprising adaptors added thereto may be cloned into a vector using the adaptor sequences, and primers that can hybridize to particular regions in such vector may be used, so as to amplify the genomic DNA fragment. An example of an amplification reaction of the genomic DNA fragment with the use of primers is PCR.

When genomic DNA is digested with a plurality of restriction enzymes and a plurality of adaptors corresponding to relevant restriction enzymes are ligated to the genomic DNA fragments, adaptors would be ligated to all genomic DNA fragments resulting from the treatment with the plurality of restriction enzymes. In such a case, primer-binding sequences contained in the adaptors may be used to perform a nucleic acid amplification reaction. Thus, all resulting genomic DNA fragments can be amplified.

When genomic DNA is digested with a plurality of restriction enzymes and an adaptor corresponding to a restriction enzyme selected from among the plurality of restriction enzymes used or adaptors corresponding to a subset of restriction enzymes selected from among the plurality of restriction enzymes used are ligated to the genomic DNA fragments, alternatively, the genomic DNA fragments comprising the recognition sequences for the selected restriction enzymes at both ends thereof can be selectively amplified among the resulting genomic DNA fragments.

Subsequently, nucleotide sequences of the amplified genomic DNA fragments are determined (Step 1e), one or more regions comprising a base length shorter than that of the genomic DNA fragment and corresponding to at least a part of the genomic DNA fragment are identified, and the one or more identified regions are designed as probes in strawberry cultivars (Step 1f). A method for determining nucleotide sequences of genomic DNA fragments is not particularly limited. For example, a region to be designed herein has a 20- to 100-base length, preferably a 30- to 90-base length, and more preferably a 50- to 75-base length as described above.

As described above, many probes are designed using genomic DNA extracted from strawberry cultivars, and oligonucleotides comprising target nucleotide sequences are synthesized on a support based on the nucleotide sequences of the designed probes. Thus, a DNA microarray can be produced. With the use of the DNA microarray produced as described above, the 1,502 markers and the 2,162 markers including the ten types of markers associated with anthracnose resistance in plants of the genus *Fragaria* as shown in SEQ ID NOs: 1 to 10 can be identified.

More specifically, the present inventors obtained the signal data with the use of the DNA microarray concerning the known strawberry cultivar Sachinoka, Strawberry Parental Line Nou-2, and hybrid progeny lines thereof (133 lines). They then obtained the genotype data from the obtained signal data, and, on the basis of the obtained genotype data, they obtained the positional information for markers in the chromosomes in accordance with a genetic distance calculation formula (Kosambi) using gene map production software (AntMap, Iwata, H., Ninomiya, S., 2006, AntMap: constructing genetic linkage maps using an ant colony optimization algorithm, Breed Sci. 56: 371-378). On the basis of the positional information for the obtained markers, in addition, a genetic map datasheet was prepared using the Mapmaker/EXP ver. 3.0 (A Whitehead Institute for Biomedical Research Technical Report, Third Edition, January, 1993). As a result, the 1,502 markers and the 2,162 markers including the ten types of markers associated with anthracnose resistance in plants of the genus *Fragaria* as shown in SEQ ID NOs: 1 to 10 are identified. [Use of markers associated with anthracnose resistance in plants of the genus *Fragaria*]

With the use of the markers associated with anthracnose resistance in plants of the genus *Fragaria*, whether or not plants of the genus *Fragaria* for which anthracnose resistance is unknown (e.g., progeny lines) have anthracnose resistance can be determined. The use of markers associated with anthracnose resistance in plants of the genus *Fragaria* includes an embodiment of the use of a method that specifically amplifies a nucleic acid fragment comprising the markers and an embodiment of the use of a DNA microarray comprising probes corresponding to the markers.

The method that specifically amplifies a nucleic acid fragment comprising markers associated with anthracnose resistance in plants of the genus *Fragaria* is a method of so-called nucleic acid amplification. Examples of methods of nucleic acid amplification include a method involving the use of a primer designed so as to specifically amplify a target nucleic acid fragment and a method of specifically amplifying a target nucleic acid fragment without the use of a primer.

A primer that specifically amplifies a target nucleic acid fragment is an oligonucleotide that can amplify a nucleic acid fragment comprising a marker associated with anthracnose resistance in plants of the genus *Fragaria* as defined above by a method of nucleic acid amplification. Methods of nucleic acid amplification involving the use of primers are not particularly limited, and any method may be employed, provided that a nucleic acid fragment is amplified. A representative example is a polymerase chain reaction (PCR). Examples of other methods include, but are not limited to, conventional techniques, such as rolling circle amplification (RCA), cycling probe technology (CPT), isothermal and chimeric-primer-initiated amplification of nucleic acids (ICAN), loop-mediated isothermal amplification of DNA (LAMP), strand displacement amplification (SDA), nucleic-acid-sequence-based amplification (NASBA), and transcription-mediated amplification (TMA).

When PCR is selected from among such nucleic acid amplification reactions, for example, a pair of primers are designed so as to sandwich markers associated with anthracnose resistance in plants of the genus *Fragaria* in the chromosome of the plant of the genus *Fragaria*. When the LAMP method is employed, 4 types of primers are designed so as to sandwich the markers associated with anthracnose resistance in plants of the genus *Fragaria* in the chromosome of plants of the genus *Fragaria*.

A method of nucleic acid amplification to be performed without the use of a primer is not particularly limited, and an example thereof is a method of ligase chain reaction (LCR). When the method of LCR is employed, a plurality of oligonucleotides that hybridize to nucleic acid fragments containing the markers associated with anthracnose resistance in plants of the genus *Fragaria* are designed.

When the markers associated with anthracnose resistance in plants of the genus *Fragaria* are present in the target plants of the genus *Fragaria*, as described above, nucleic acid fragments containing the markers can be obtained as amplification products according to methods of nucleic acid amplification. When a nucleic acid fragment of interest is amplified via a method of nucleic acid amplification using, as a template, the chromosome extracted from the target plant of the genus *Fragaria*, in other words, it can be determined that the target plant of the genus *Fragaria* has anthracnose resistance.

Methods for detecting an amplified nucleic acid fragment are not particularly limited. Examples thereof include a method in which a solution resulting after the amplification reaction is subjected to agarose electrophoresis, and a fluorescent intercalator, such as ethidium bromide or SYBR green, is allowed to bind thereto, so as to observe specific fluorescence, a method in which a fluorescent intercalator is added to a solution used for nucleic acid amplification, so as to detect fluorescence after the amplification reaction, and a method in which nucleic acid amplification is carried out with the use of a fluorescence-labeled primer, so as to detect fluorescence after the amplification reaction.

When the markers associated with anthracnose resistance in plants of the genus *Fragaria* are detected via a method of nucleic acid amplification, an amplified fragment containing such markers can contain, for example, 30 to 10,000, preferably 50 to 5,000, and more preferably 70 to 2,000 nucleotides, although the number of nucleotides would vary depending on the principle of the method of nucleic acid amplification.

When evaluating the anthracnose resistance of plants of the genus *Fragaria*, a plurality of markers associated with anthracnose resistance in plants of the genus *Fragaria* may be detected. Specifically, a plurality of regions selected from nucleic acid regions sandwiched between the nucleotide sequence as shown in SEQ ID NO: 1 and the nucleotide sequence as shown in SEQ ID NO: 10 in the chromosome of plants of the genus *Fragaria* may be designated as the markers associated with anthracnose resistance in plants of the genus *Fragaria*, and the plurality of markers associated with anthracnose resistance in plants of the genus *Fragaria* may be detected. For example, a plurality of regions selected from among 10 regions consisting of nucleotide sequences as shown in SEQ ID NOs: 1 to 10 may be designated as the markers associated with anthracnose resistance in plants of the genus *Fragaria*, and the plurality of regions may be detected.

For example, the region comprising the nucleotide sequence as shown in SEQ ID NO: 7 (IA200826) and the region comprising the nucleotide sequence as shown in SEQ ID NO: 8 (IA202631) may be designated as the markers associated with anthracnose resistance in plants of the genus *Fragaria*, and these regions may be subjected to nucleic acid amplification, so as to determine the presence or absence of the markers associated with anthracnose resistance in plants of the genus *Fragaria*. Alternatively, a region sandwiched between the region comprising the nucleotide sequence as shown in SEQ ID NO: 7 (IA200826) and the region comprising the nucleotide sequence as shown in SEQ ID NO: 8 (IA202631) may be designated as the marker associated with anthracnose resistance in plants of the genus *Fragaria*, and the region may be subjected to nucleic acid amplification, so as to determine the presence or absence of the marker associated with anthracnose resistance in plants of the genus *Fragaria*.

According to an embodiment in which a DNA microarray comprising probes corresponding to the markers associated with anthracnose resistance in plants of the genus *Fragaria* is used, the probes are oligonucleotides that can hybridize specifically to the markers associated with anthracnose resistance in plants of the genus *Fragaria* as defined above under stringent conditions. Such an oligonucleotide can be designed as, for example, a partial region comprising 10, 15, 20, 25, 30, 35, 40, 45, 50, or more continuous nucleotides in the nucleotide sequence of the marker associated with anthracnose resistance in plants of the genus *Fragaria* as defined above or a complementary strand thereof or the entire region of the nucleotide sequence. The DNA microarray comprising probes may be, for example, a microarray comprising planar substrate of glass or silicone as a carrier, a bead array comprising microbeads as carriers, or a three-dimensional microarray comprising probes immobilized on the inner wall of a hollow fiber.

With the use of the DNA microarray thus produced, whether or not a plant of the genus *Fragaria* with unknown phenotypic characteristics with regard to anthracnose resistance (e.g., a progeny line) exhibits a phenotype indicating excellent anthracnose resistance can be determined. Alternatively, the marker associated with anthracnose resistance in plants of the genus *Fragaria* may be detected in accordance with a conventional technique, and the target plants of the genus *Fragaria* may be tested for excellent anthracnose resistance by a method other than the method involving the use of a DNA microarray. An example of a method other than the method involving the use of a DNA microarray that can be employed is so-called FISH (fluorescence in situ hybridization) involving the use of the probes described above.

Figure 2:
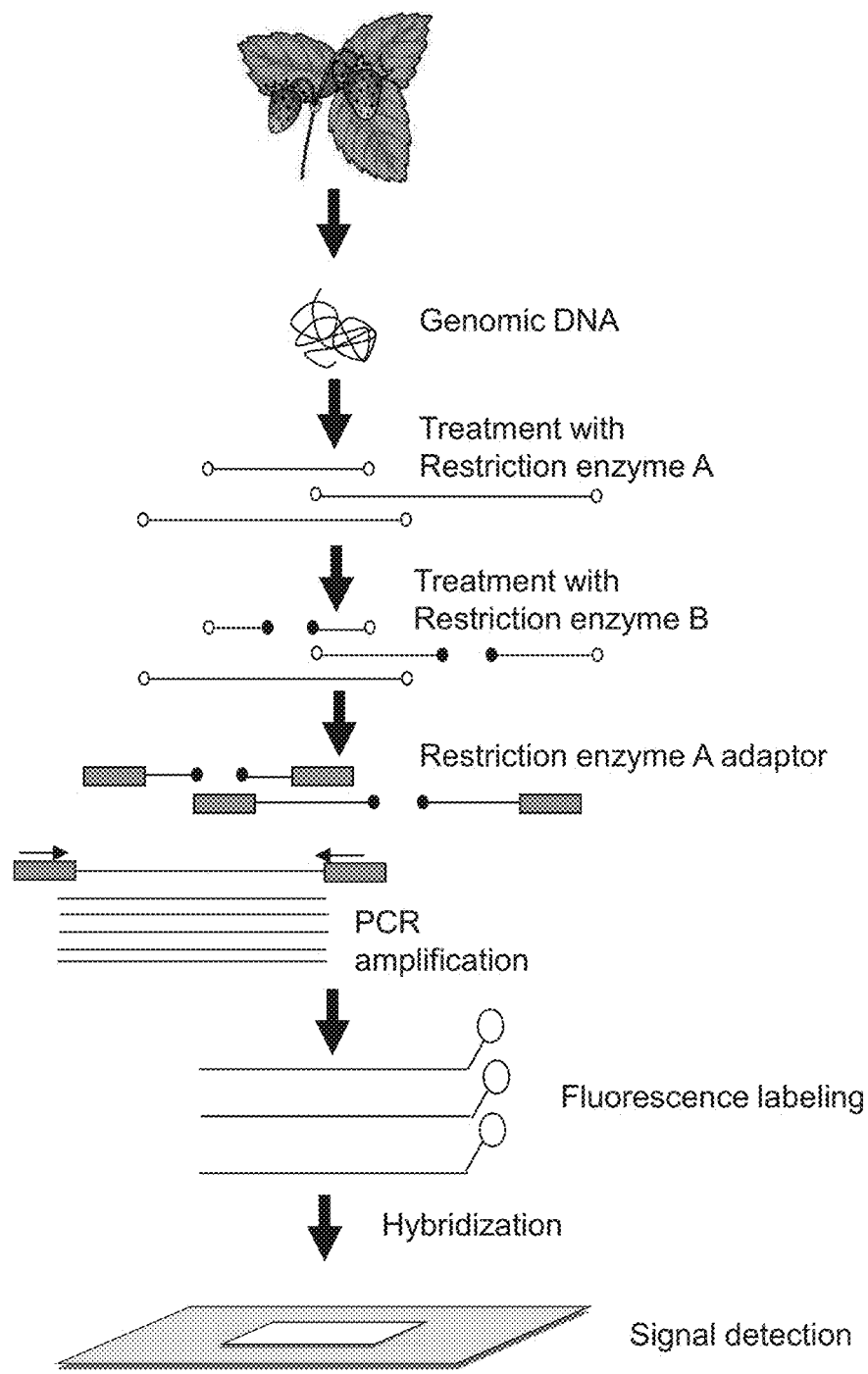
FIG. 2 schematically shows a step of signal detection using a DNA microarray.

A method involving the use of a DNA microarray is described in greater detail. As shown in FIG. 2, genomic DNA is first extracted from a target plant of the genus *Fragaria*. A target plant of the genus *Fragaria* is a plant of the genus *Fragaria* with unknown phenotypic characteristics in terms of anthracnose resistance (e.g., a progeny line) and/or a parent plant of the genus *Fragaria* used when producing a progeny line, and thus is used a subject to be determine whether or not the plant of the genus *Fragaria* has excellent anthracnose resistance.

Subsequently, the extracted genomic DNA is digested with the restriction enzyme used when preparing the DNA microarray described in the [Identification of markers in plants of the genus *Fragaria*] section above, so as to prepare a plurality of genomic DNA fragments. The resulting genomic DNA fragments are then ligated to adaptors used when preparing the DNA microarray. The genomic DNA fragments comprising adaptors added to the both ends are then amplified using the primers used when preparing the DNA microarray. Thus, the genomic DNA fragments derived from the target plant of the genus *Fragaria* corresponding to the genomic DNA fragment amplified in Step 1 d when preparing a DNA microarray can be amplified.

In this step, among the genomic DNA fragments comprising adaptors added thereto, specific genomic DNA fragments may be selectively amplified. When a plurality of adaptors corresponding to the plurality of restriction enzymes are used, for example, genomic DNA fragments comprising specific adaptors added thereto can be selectively amplified. When genomic DNA is digested with a plurality of restriction enzymes, adaptors are selectively added to the genomic DNA fragments having protruding ends corresponding to specific restriction enzymes among the resulting genomic DNA fragments. Thus, genomic DNA fragments comprising the adaptors added thereto can be selectively amplified. By selectively amplifying specific genomic DNA fragments, as described above, these fragments can be concentrated.

Subsequently, the amplified genomic DNA fragments are labeled. Any conventional material may be used as a label. Examples of labels that can be used include fluorescent molecules, pigment molecules, and radioactive molecules. This step can be omitted with the use of a labeled nucleotide in the step of genomic DNA fragment amplification. That is, a genomic DNA fragment is amplified with the use of a labeled nucleotide in the above step, so that the amplified DNA fragment is labeled.

Subsequently, a labeled genomic DNA fragment is brought into contact with a DNA microarray under given conditions, so as to allow a probe immobilized on a DNA microarray to hybridize to the labeled genomic DNA fragment. It is preferable that hybridization be carried out under highly stringent conditions. Under highly stringent conditions, whether or not the marker associated with anthracnose resistance in plants of the genus *Fragaria* is present in the target plant of the genus *Fragaria* can be determined with higher accuracy. Stringent conditions can be adjusted based on reaction temperature and salt concentration. Specifically, higher stringency can be realized by increasing temperature or decreasing salt concentration. When a probe comprising 50 to 75 nucleotides is used, for example, hybridization can be carried out at 40° C. to 44° C. in 0.2% SDS and 6×SSC, so that higher stringency can be realized.

Hybridization between a probe and a labeled genomic DNA fragment can be detected based on a label. After the hybridization reaction between the labeled genomic DNA fragment and the probes, specifically, unreacted genomic DNA fragments or the like are washed, and a label bound to the genomic DNA fragment that had specifically hybridized to the probes are then observed. In the case that the label is a fluorescent material, for example, the fluorescent wavelength thereof is detected. When a label is a pigment molecule, the pigment wavelength thereof is detected. More specifically, apparatuses such as fluorescence detectors or image analyzers used for conventional DNA microarray analysis can be used.

Using the method involving nucleic acid amplification or the method involving the use of a DNA microarray, as described above, whether or not the target plant of the genus *Fragaria* has the marker associated with anthracnose resistance in plants of the genus *Fragaria* can be determined. If markers linked to trait of excellent anthracnose resistance among markers associated with anthracnose resistance in plants of the genus *Fragaria* are present, the target plant can be determined to be of a line or variety excellent in anthracnose resistance. If no marker linked to reduced anthracnose resistance among markers associated with anthracnose resistance in plants of the genus *Fragaria* is present, the target plant can be determined to be of a line or variety excellent in anthracnose resistance.

According to the method described above, in particular, it is not necessary to have the target plant of the genus *Fragaria* grow to an extent that allows it to be subjected to an actual test as to anthracnose resistance. For example, seeds of progeny lines or young seedlings germinated from such seeds can be used. With the use of the markers associated with anthracnose resistance in plants of the genus *Fragaria*, accordingly, cost of the field for growing the target plant of the genus *Fragaria*, and cost for growing the plant can be reduced to a significant extent. Also, the use of markers associated with anthracnose resistance in plants of the genus *Fragaria* eliminates the need to actually infect plants with microorganisms causing anthracnose (i.e., *Glomerella cingulate* and/or *Colletotrichum acutatum*). Thus, expenditures required for equipment such as a large-scale greenhouse for an exclusive purpose, a field for an exclusive purpose, or a facility isolated from the outside can be reduced.

When producing new varieties of the plants of the genus *Fragaria*, it is particularly preferable that several tens of thousands of types of hybrid species be first produced via crossing and evaluation take place prior to or instead of seedling selection with the use of the markers associated with anthracnose resistance in plants of the genus *Fragaria*. Thus, the number of plants to be grown so as to produce desirable varieties in the actual field can be reduced to a significant extent, and the labor and expenditures required for the production of new varieties of plants of the genus *Fragaria* can be reduced to a significant extent.

When producing new varieties of plants of the genus *Fragaria*, alternatively, the presence or absence of the markers associated with anthracnose resistance in plants of the genus *Fragaria* in the parent varieties to be used for crossing is first evaluated, and parent varieties with excellent anthracnose resistance can be selected. By producing progeny lines with the preferential use of parent varieties with excellent anthracnose resistance, progeny lines with excellent anthracnose resistance can develop at high frequency. Thus, the number of plants necessary to cultivate in order to produce superior lines can be reduced to a significant extent, and the labor and expenditures required for the production of new plant varieties of the genus *Fragaria* can be reduced to a significant extent.

EXAMPLES

Hereafter, the present invention is described in greater detail with reference to the examples, although the technical scope of the present invention is not limited to these examples.

1. Preparation of DNA Microarray Probe
(1) Materials

The strawberry cultivars: Sachinoka and Strawberry Parental Line Nou-2, were used.

(2) Treatment with Restriction Enzyme

Genomic DNA was extracted from these strawberry cultivars by the cetyl trimethyl ammonium bromide (CTAB) method. The extracted genomic DNA (180 ng) was treated with the PstI restriction enzyme (6 units, NEB) at 37° C. for 1 hour. Thereafter, the BstNI restriction enzyme (5 units, NEB) was added to the genomic DNA (150 ng) treated with PstI and the resultant was then treated at 60° C. for 1 hour.

(3) Ligation of Adaptor

The PstI sequence adaptors (5'-CACGATG-GATCCAGTGCA-3' (SEQ ID NO: 11) and 5'-CTGGATC-CATCGTGCA-3' (SEQ ID NO: 12)) and T4 DNA ligase (800 units, NEB) were added to the genomic DNA fragment (120 ng) treated in (2) above, and the resultant was subjected to ligation at 16° C. for 4 hours or longer. Thus, adaptors were selectively added to the genomic DNA fragments comprising the PstI recognition sequences at both ends thereof among the genomic DNA fragments treated in (2) above.

(4) Amplification by PCR

The PstI sequence adaptor recognition primer (5'-GATG-GATCCAGTGCAG-3' (SEQ ID NO: 13)) and Taq polymerase (PrimeSTAR, 1.25 units, Takara Bio Inc.) were added to the genomic DNA fragment (15 ng) comprising adaptors obtained in (3) above, and the genomic DNA fragment was amplified by PCR (30 cycles of 98° C. for 10 seconds, 55° C. for 15 seconds, and 72° C. for 1 minute, treatment at 72° C. for 3 minutes, followed by storage at 4° C.).

(5) Acquisition of Genome Sequence

The nucleotide sequence of the genomic DNA fragment amplified by PCR in (4) above was determined using GAII (Illumina).

(6) Design of Probes and Preparation of DNA Microarray

On the basis of the genome sequence information acquired in (5) above, 50 to 75 bp probes were designed. On the basis of the nucleotide sequence information of the designed probes, a DNA microarray comprising these probes was produced.

2. Acquisition of Signal Data Using DNA Microarray
(1) Materials

The strawberry cultivars: Sachinoka, Strawberry Parental Line Nou-2 and the 133 hybrid progeny lines were used.

(2) Treatment with Restriction Enzyme

Genomic DNA was extracted from the strawberry cultivars indicated above and the hybrid progeny lines by the CTAB method. The extracted genomic DNA (180 ng) was treated with the PstI restriction enzyme (6 units, NEB) at 37° C. for 1 hour. Thereafter, the BstNI restriction enzyme (5 units, NEB) was added to the genomic DNA (150 ng) treated with PstI and the resultant was then treated at 60° C. for 1 hour.

(3) Ligation of Adaptor

The PstI sequence adaptors (5'-CACGATG-GATCCAGTGCA-3' (SEQ ID NO: 11) and 5'-CTGGATC-CATCGTGCA-3' (SEQ ID NO: 12)) and T4 DNA ligase (800 units, NEB) were added to the genomic DNA fragment (120 ng) treated in (2) above, and the resultant was subjected to ligation at 16° C. for 4 hours or longer. Thus, adaptors were selectively added to the genomic DNA fragments comprising the PstI recognition sequences at both ends thereof among the genomic DNA fragments treated in (2) above.

(4) Amplification by PCR

The PstI sequence adaptor recognition primer (5'-GATG-GATCCAGTGCAG-3' (SEQ ID NO: 13)) and Taq polymerase (PrimeSTAR, 1.25 units, Takara Bio Inc.) were added to the genomic DNA fragment (15 ng) comprising adaptors obtained in (3) above, and the genomic DNA fragment was amplified by PCR (30 cycles of 98° C. for 10 seconds, 55° C. for 15 seconds, and 72° C. for 1 minute, treatment at 72° C. for 3 minutes, followed by storage at 4° C.).

(5) Labeling

The PCR-amplified fragment obtained in (4) above was purified through a column (Qiagen), and a labeled sample was then prepared using a NimbleGen One-Color DNA Labeling kit in accordance with the NimbleGen Arrays User's Guide.

(6) Hybridization and Signal Detection

Hybridization was carried out in accordance with the NimbleGen Arrays User's Guide using the labeled sample obtained in (5) above and the DNA microarray prepared in 1. above. Signal from the label was detected.

3. Identification of QTL Associated with Anthracnose Resistance in Plants of the Genus *Fragaria* and Development of Markers (1) Preparation of Genetic Map Data From the signal data of Sachinoka, Strawberry Parental Line Nou-2, and the hybrid progeny line 133, the genotype data of possible Sachinoka-type 1,502 markers and possible Strawberry Parental Line Nou-2-type 2,162 markers were obtained. On the basis of the genotype data, the positional information concerning markers in the chromosomes was obtained in accordance with the genetic distance calculation formula (Kosambi) using the gene map production software (AntMap, Iwata, H., Ninomiya, S., 2006, AntMap: constructing genetic linkage maps using an ant colony optimization algorithm, Breed Sci. 56: 371-378). Thus, the gene mapping data of the markers were obtained.

(2) Acquisition of Data for Strawberry Anthracnose Test

Sachinoka, Strawberry Parental Line Nou-2, and the clones from runner propagation of 103 hybrid progeny lines were designated as test lines. Groups of the test lines each consisting of 5 individuals were cultivated 3 repeated times. The lower lobes were removed, so as to adjust the number of expanded leaves to 3 or 4 up to 2 days before inoculation.

The strawberry anthracnose strains (*Glomerella cingulata*) possessed by the Institute of Vegetable and Tea Science, the National Agriculture and Food Research Organization were shake-cultured in PS liquid media (20 g of mashed potatoes and 2% sucrose relative to 1,000 ml) at 120 rpm for 5 days. After the culture solution was filtered through gauze, the solution in which the conidial density was adjusted to $10^5$ conidia/ml was designated as the inoculum (a conidial suspension). Inoculation was initiated at 3:00 pm on Sep. 19, 2012, when the temperature began to decrease, by spraying the prepared inoculum (a conidial suspension) on plants so as to wet the entire plants with the use of a battery-operated, over-the-shoulder-type power sprayer without the addition of a spreading agent or the like.

Figure 3:
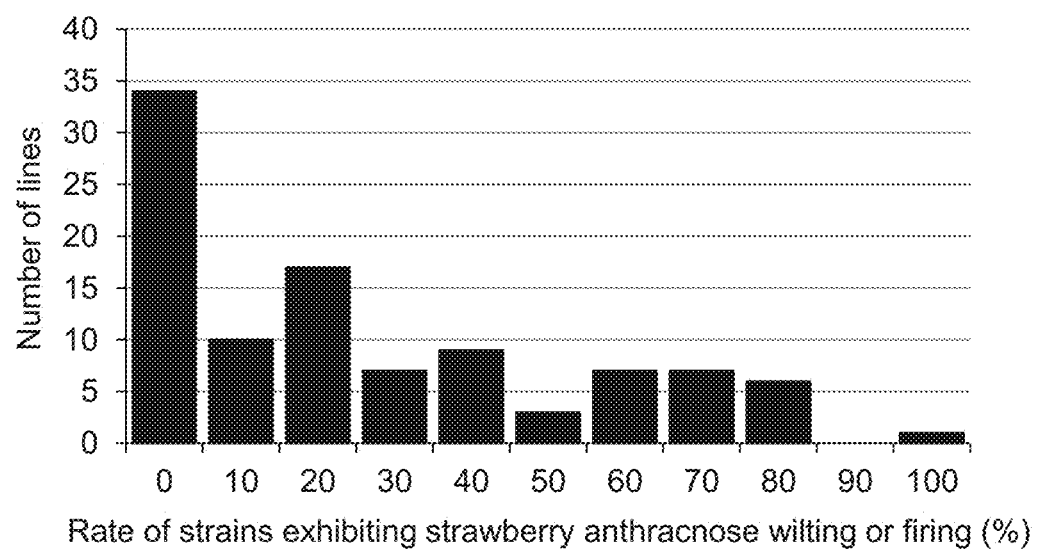
FIG. 3 is a characteristic diagram showing the data on anthracnose resistance of the plant varieties and lines of the genus *Fragaria* used in the examples tested on Oct. 19, 2012.

Thereafter, the disease was induced in a glass chamber with a light-shielding cheesecloth lining. The glass chamber was closed tightly and it was kept in humid conditions from the day of inoculation to the daytime on the following day. Thereafter, a roof window and a side window were allowed to automatically close or open (25° C.) and the temperature was controlled automatically. The strains affected with strawberry anthracnose were determined in terms of the rate of the strains exhibiting wilting or firing among all varieties and lines on October 19. The results of determination are shown in FIG. 3.

(3) Analysis of Quantitative Trait Loci (QTL)

Figure 4:
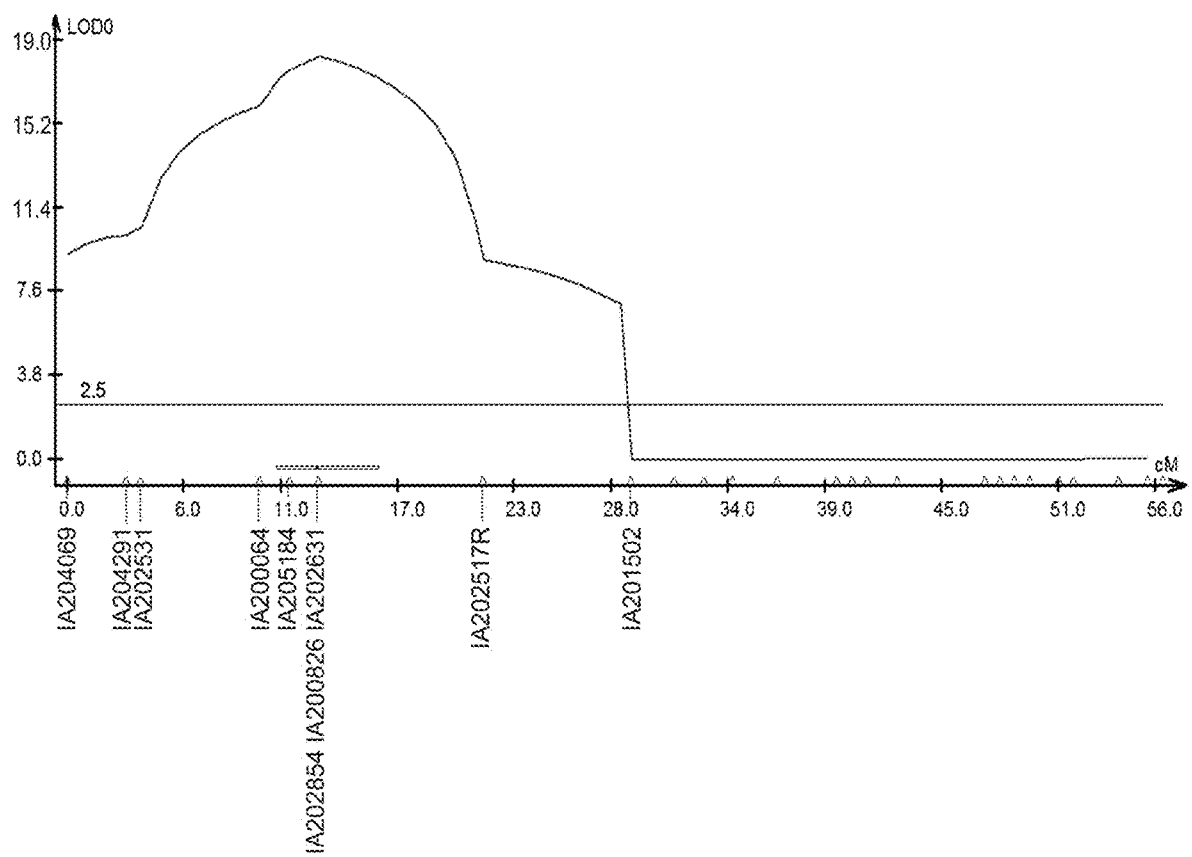
FIG. 4 is a characteristic diagram showing the results of QTL analysis concerning anthracnose resistance (the 23rd linkage group of Strawberry Parental Line Nou-2).
Figure 5:
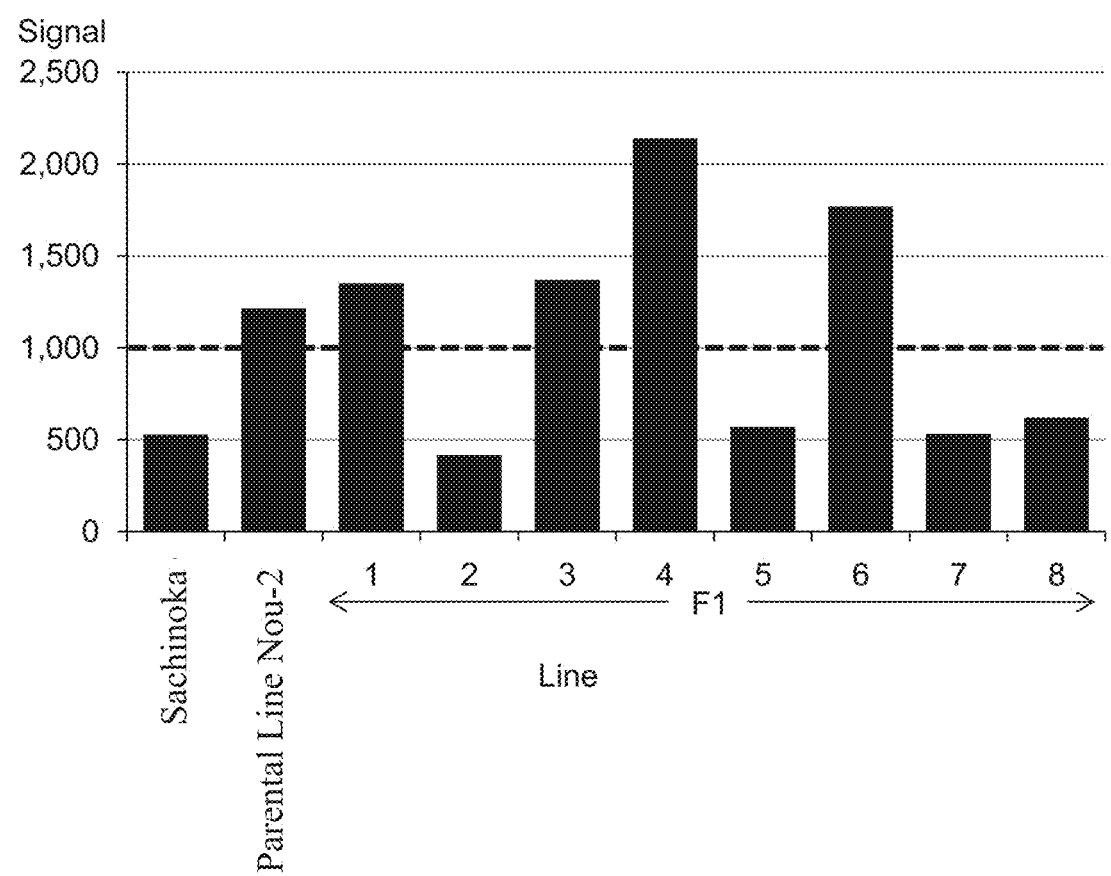
FIG. 5 is a characteristic diagram showing the IA204069 signal level for each line.
Figure 6:
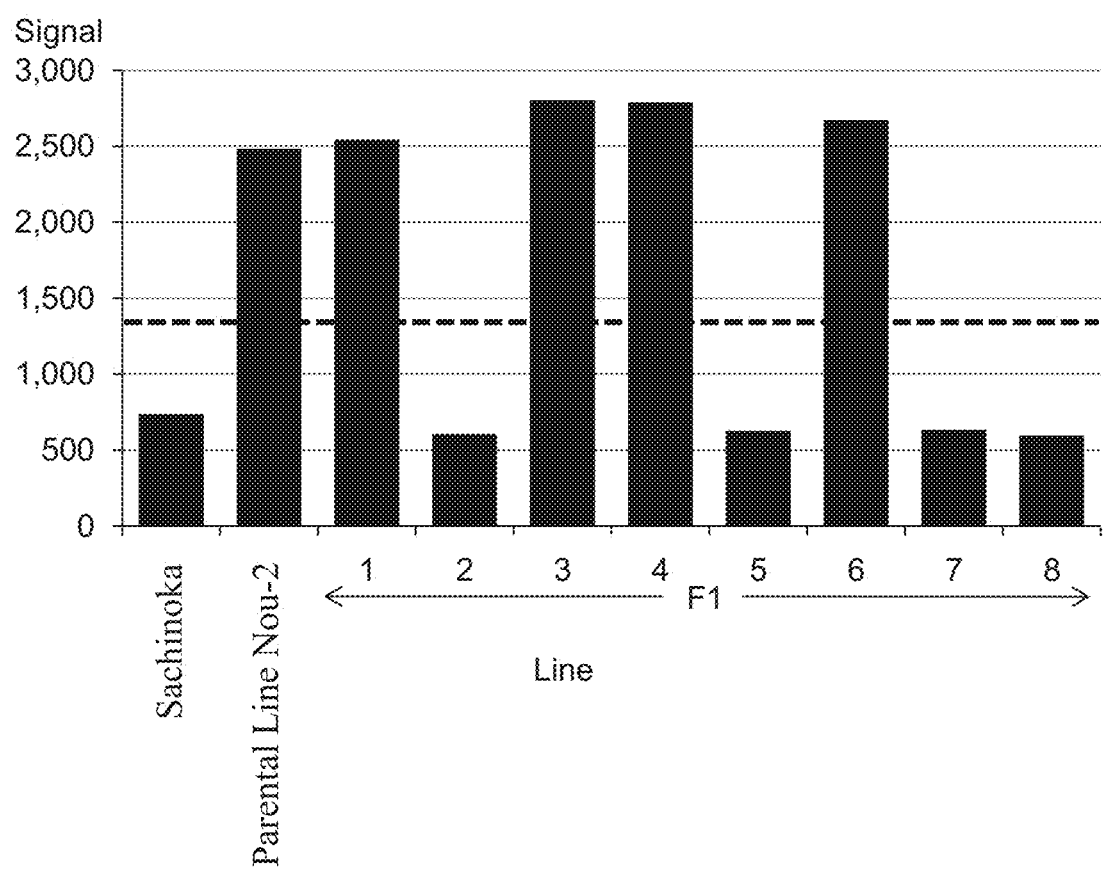
FIG. 6 is a characteristic diagram showing the IA204291 signal level for each line.
Figure 7:
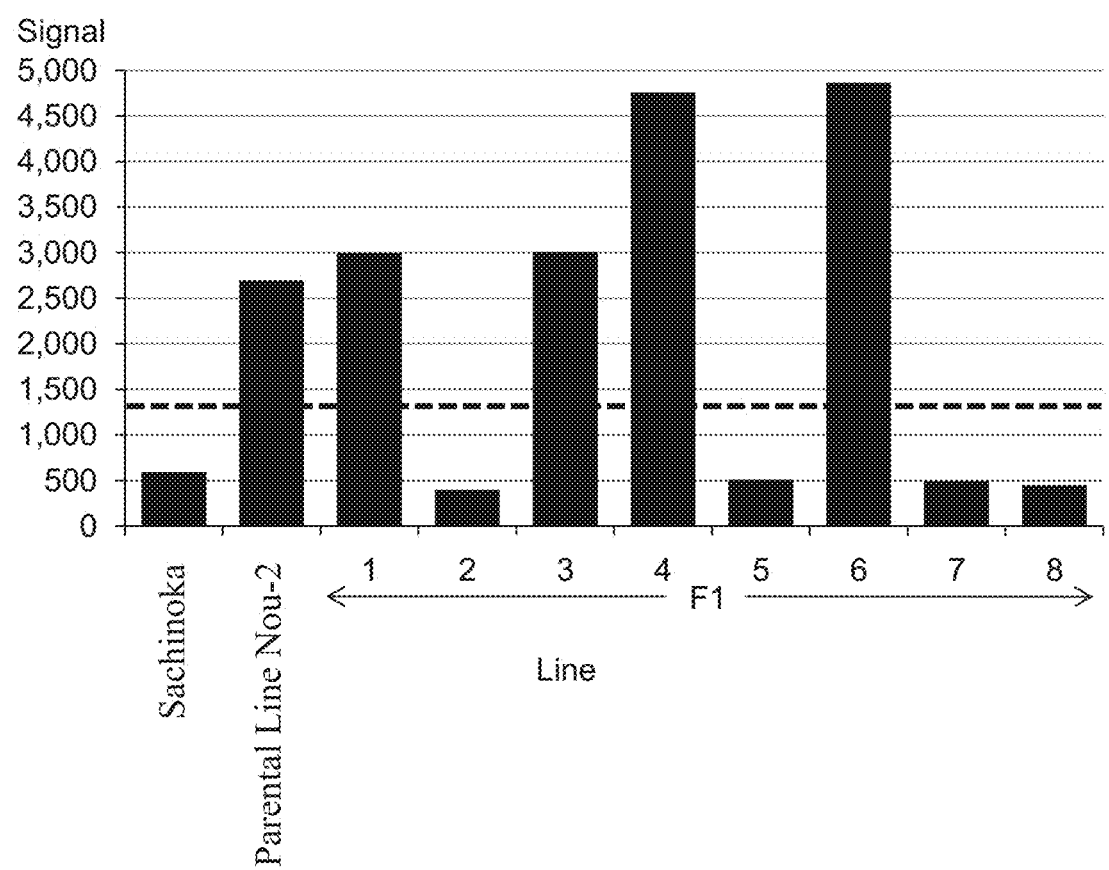
FIG. 7 is a characteristic diagram showing the IA202531 signal level for each line.
Figure 8:
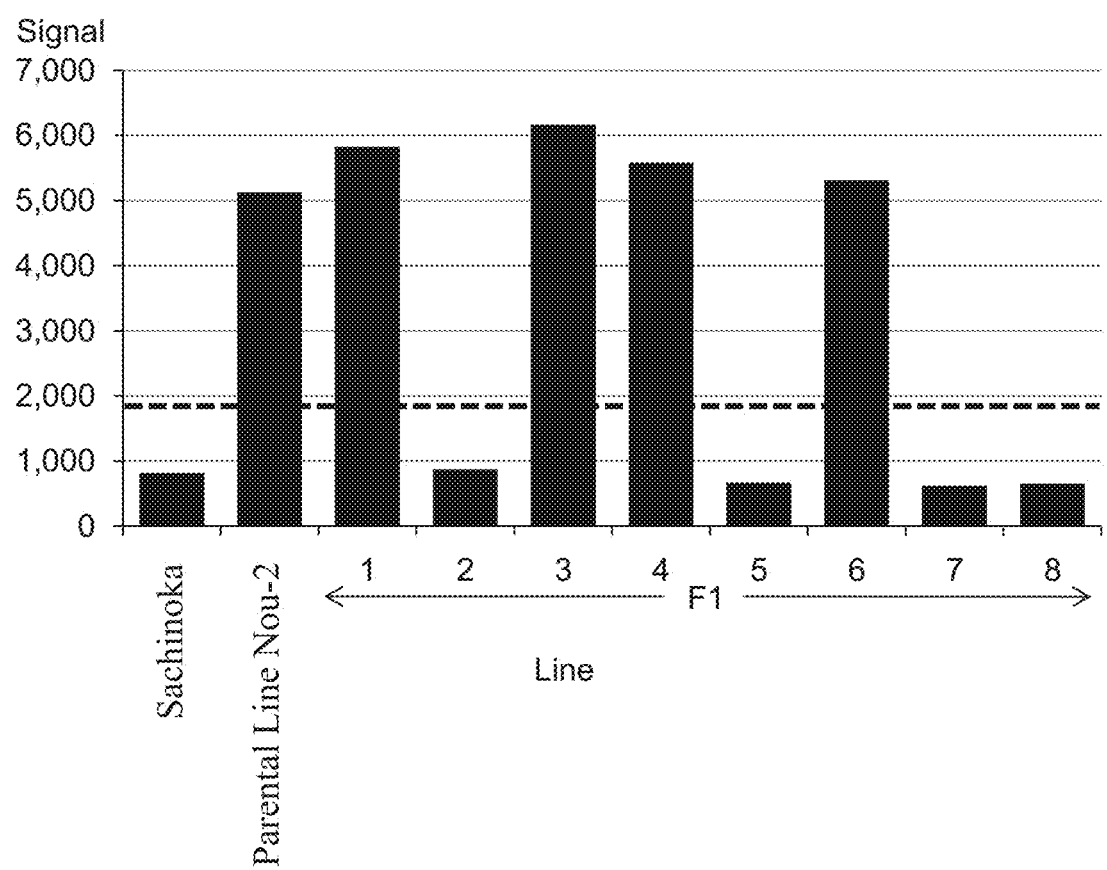
FIG. 8 is a characteristic diagram showing the IA200064 signal level for each line.
Figure 9:
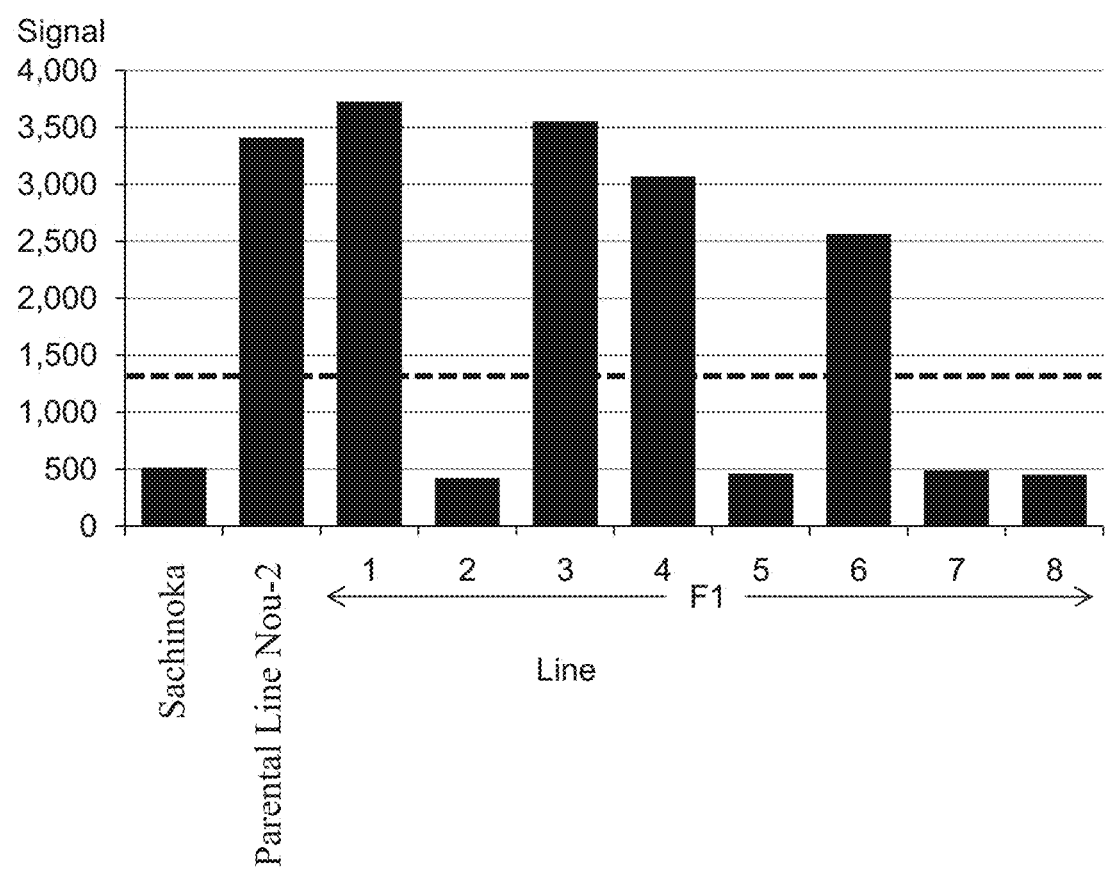
FIG. 9 is a characteristic diagram showing the IA205184 signal level for each line.
Figure 10:
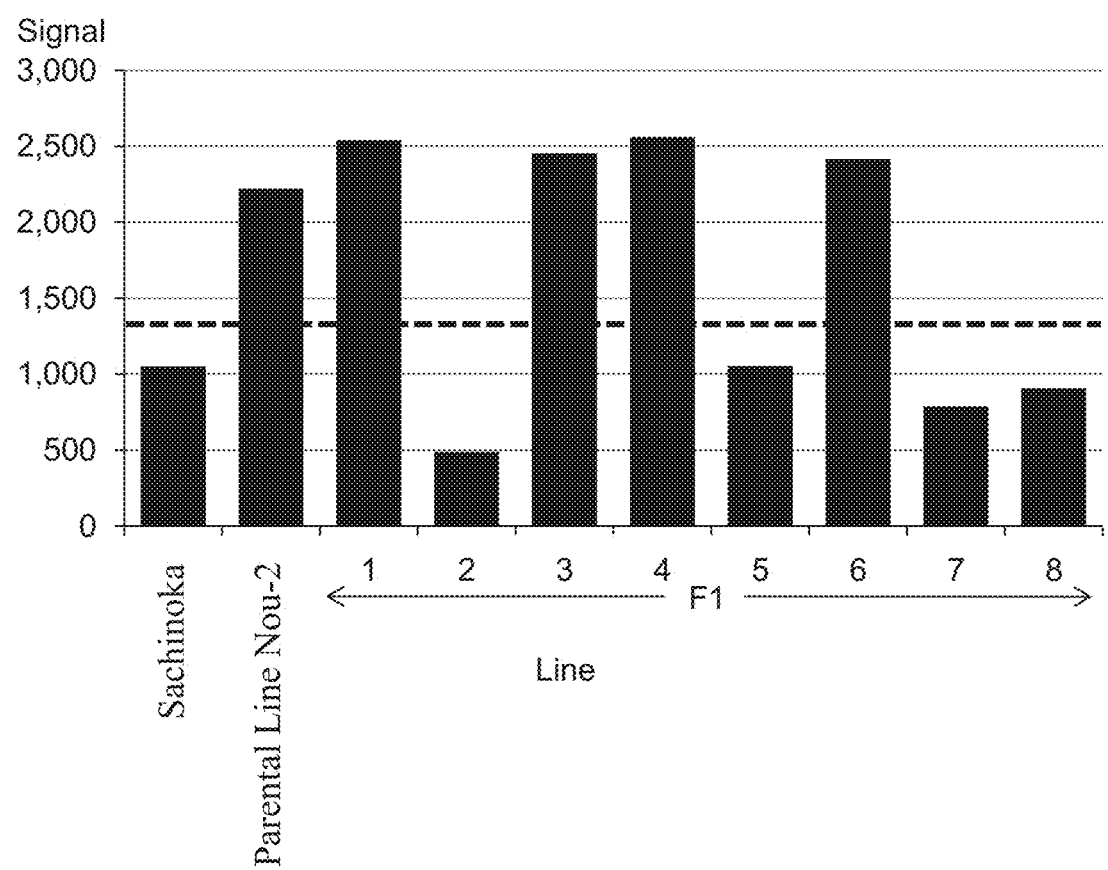
FIG. 10 is a characteristic diagram showing the IA202854 signal level for each line.
Figure 11:
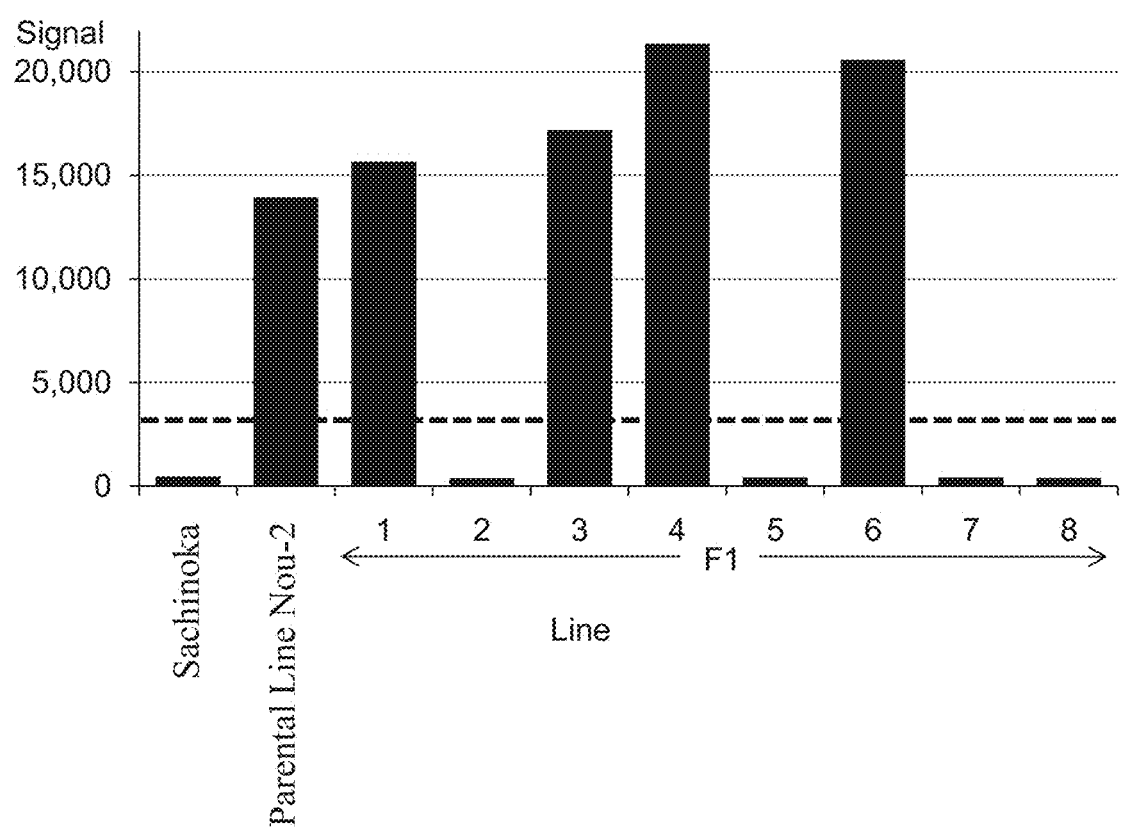
FIG. 11 is a characteristic diagram showing the IA200826 signal level for each line.
Figure 12:
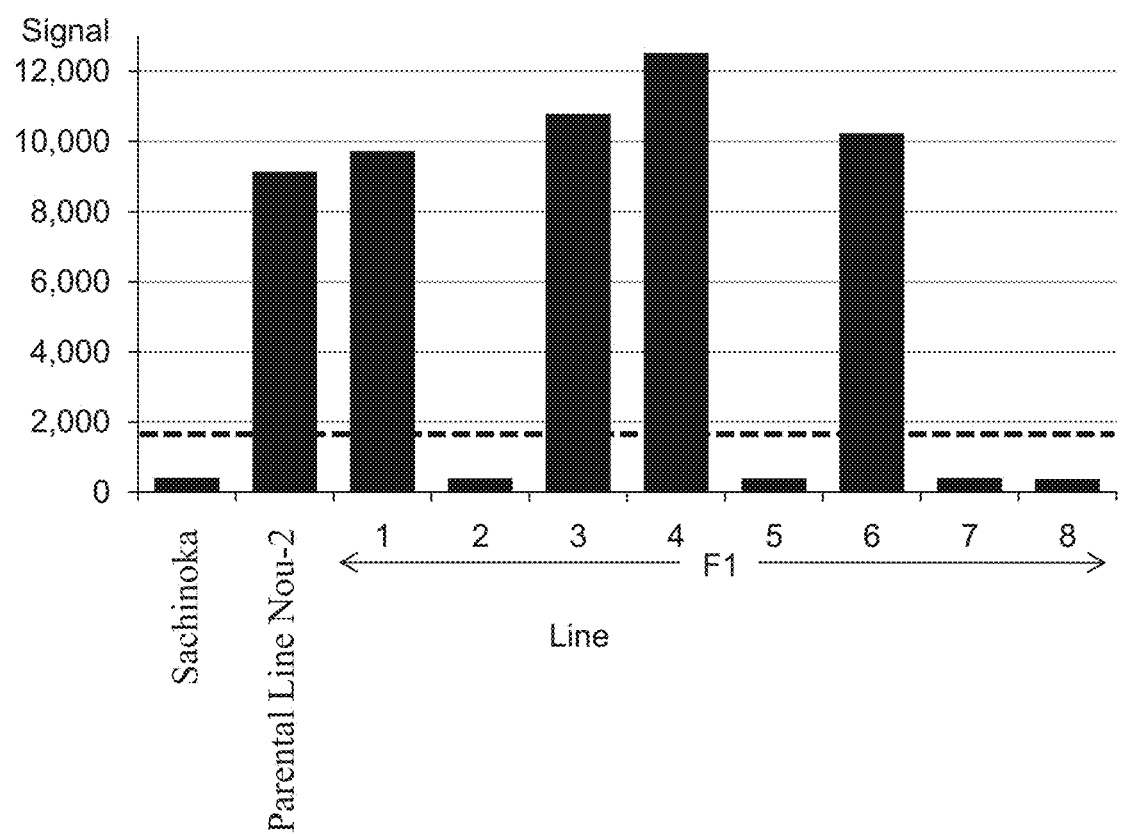
FIG. 12 is a characteristic diagram showing the IA202631 signal level for each line.
Figure 13:
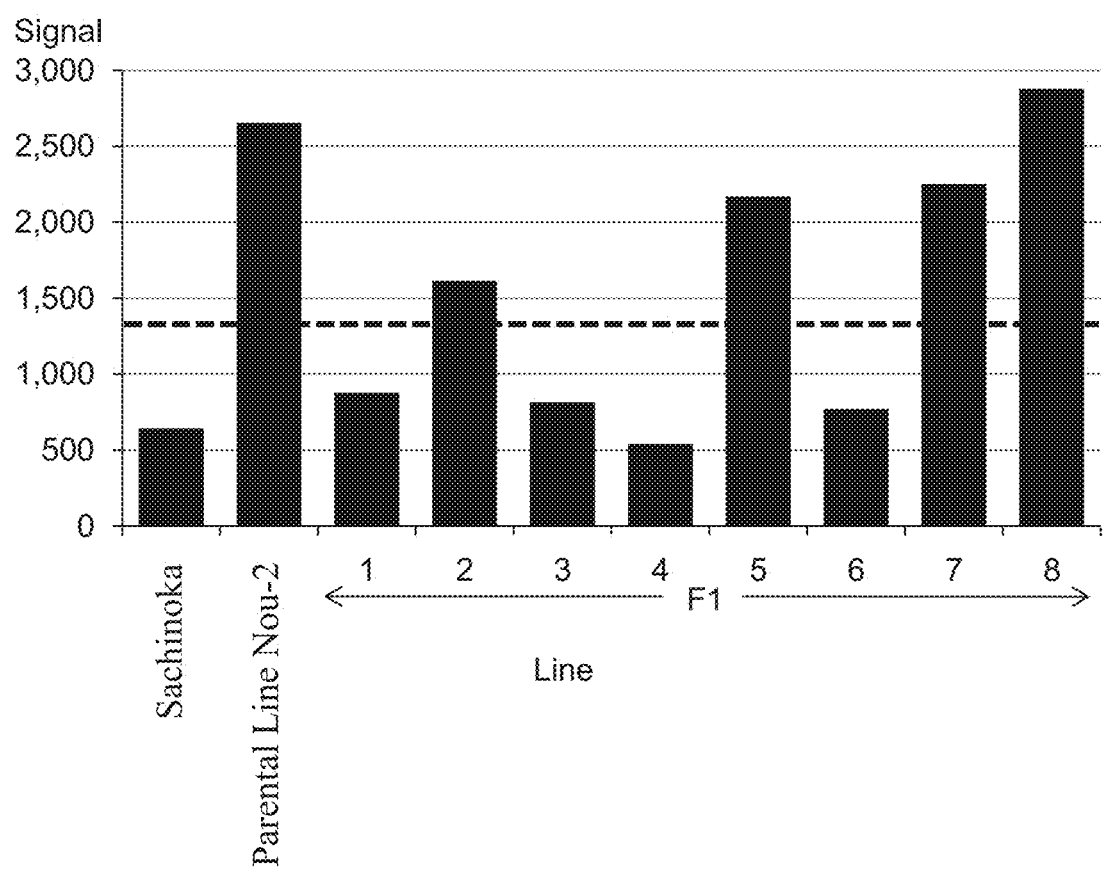
FIG. 13 is a characteristic diagram showing the IA202517R signal level for each line.
Figure 14:
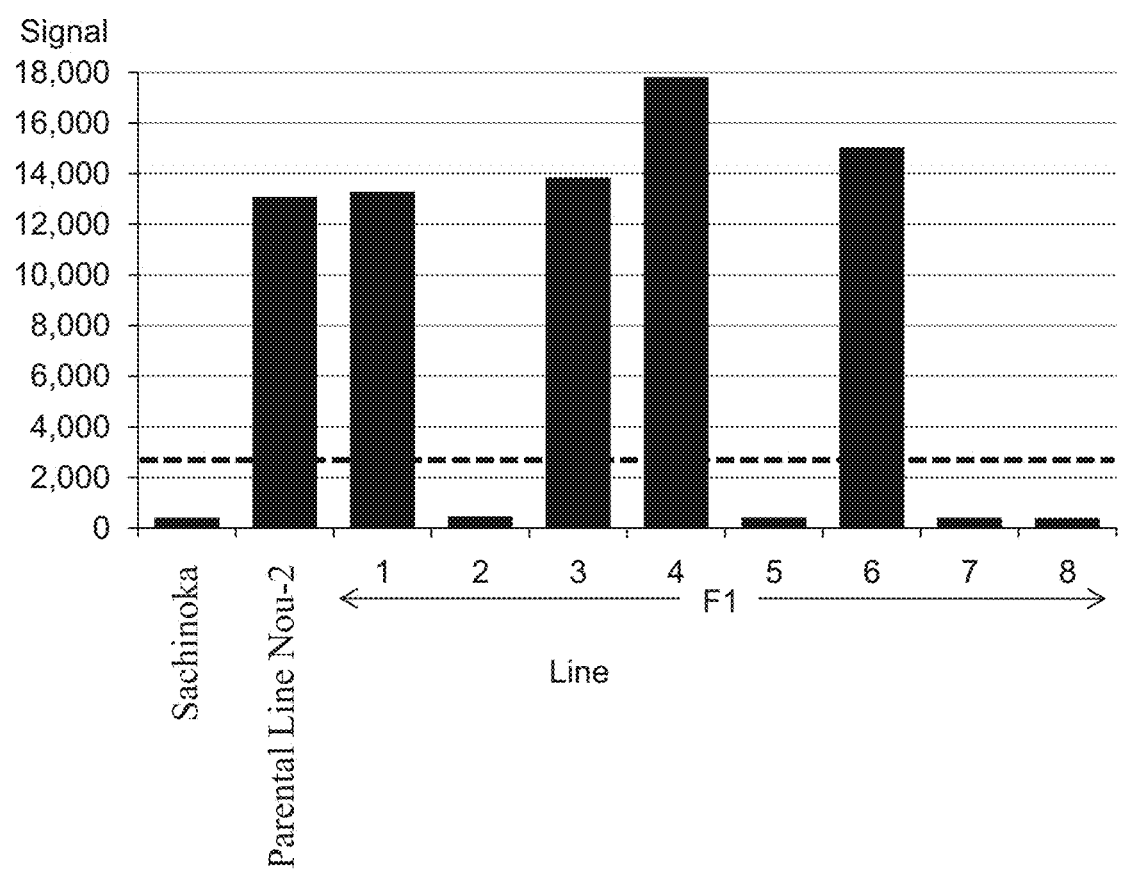
FIG. 14 is a characteristic diagram showing the IA201502 signal level for each line.

On the basis of the genetic map data obtained in (1) above and the results of strawberry anthracnose test obtained in (2) above (i.e., the rate of strains exhibiting wilting or firing), QTL analysis was carried out by the composite interval mapping (CIM) method with the use of the gene analysis software (QTL Cartographer, Wang S., C. J. Basten, and Z.-B. Zeng, 2010, Windows QTL Cartographer 2.5. Department of Statistics, North Carolina State University, Raleigh, N.C.). The LOD threshold was designated to be 2.5. As a result, as shown in FIG. 4, a peak indicating the presence of the gene associated with strawberry anthracnose resistance (LOD value: 18.3) was observed in a region between the IA204069 marker and the IA201502 marker in the 23rd linkage group of Strawberry Parental Line Nou-2. The peak was identified as shown in Table 2, and the peak indicates the presence of a causal gene (or causal genes) capable of improving anthracnose resistance.

TABLE 2

| Variety | Linkage group | Position (cM) | Range (cM) | Adjacent marker | LOD | Effects* (%) | Contribution (%) |
|---|---|---|---|---|---|---|---|
| Parental Line Nou-2 | 23 | 12.9 | 29.0 | IA204069-IA201502 | 18.3 | −38.4 | 45.0 |

*Rate of the strains exhibiting wilting or firing (%)

In Table 2, the column of the effects (%) indicates the rate of strains exhibiting anthracnose wilting or firing. If the numeral value indicating the effects (%) is a negative value, accordingly, QTL indicated by such value is linked to a trait that improves the anthracnose resistance.

As shown in FIG. 4, a marker located in the vicinity of such peak is inherited in linkage with a causal gene (or causal genes) capable of improving the anthracnose resistance. This indicates that such marker may be used as the marker associated with anthracnose resistance in plants of the genus *Fragaria*. Specifically, the 10 types of markers shown in FIG. 4 were found to be usable as markers associated with anthracnose resistance in plants of the genus *Fragaria*.

Table 3 shows the nucleotide sequences of the probes prepared in this example and the signal value thresholds.

the IA202531 marker and the IA200064 marker were prepared on the basis of the sequence information thereof.

TABLE 3

| SEQ ID NO | Marker Name | Probe sequence | Signal threshold |
|---|---|---|---|
| 11 | IA204069 | GCGTTACTAATTGATATTGGGTTTACAATAAGTATCAATTTGCTAAAGCTAGCTACAACAGCACTACAGCA | 1,000 |
| 12 | IA204291 | TGAAGTAAACCAATGGAAAAGGGCAGAAGAAATGAGACTAGAAGAGGCAAAAGTAGC | 1,400 |
| 13 | IA202531 | TGGAAGAGGTGATCCAGAGTTCTAAACTATATAGCATCACTGTTCATTTAAATCGTCACG | 1,300 |
| 14 | IA200064 | GAATAAGTTCAACATTATCAAGGAAAATGAAGCAATTTATCTCTGCAAGGTTTTAGAGGTAACAAATT | 1,900 |
| 15 | IA205184 | ATTGTTGTCTAAATAGCTGAATGAGTAATTGAGGCTATGGGCCAATGAGCCCA | 1,300 |
| 16 | IA202854 | TTTCATTTTAAACAGAAGTTTTCATTTTTCTTTATACGCCTAAGCTAAAAACTTTTATAATC | 1,300 |
| 17 | IA200826 | GTGCTGTTGTCAGTCTCATTAATACAACTGTATATAGTGATGACTGGTGCTAATCTTCTATTTCATCTG | 2,800 |
| 18 | IA202631 | TGTATGTATCTGTATCTGTATCTATCTCTCATATCTCTATGTAACTATATAAAGACAACCTCACAGCTGCACT | 1,900 |
| 19 | IA202517R | GCCGACCAGTCGCTATGTTTTTATTTTGTTCAAATTGTACGTGTGTGTCCTCAATAGTTTCTTTTCAA | 1,300 |
| 20 | IA201502 | CGTTTCTACTTCAACCGAAATATGGTACCTGCAACTGTTAATTTTGTTAAAACAACTGACAGATTA | 2,500 |

FIG. 5 to FIG. 14 show the results of detection of signals of markers from the IA204069 marker to the IA201502 marker concerning Sachinoka, Strawberry Parental Line Nou-2, and progeny lines thereof with the use of the probes shown in Table 3 ("Parental Line Nou-2" indicates the Strawberry Parental Line Nou-2 in FIG. 5 to FIG. 14), respectively. FIG. 22 shows a summary of the results of detection.

As shown in FIGS. 5 to 14 and 22, a region between the IA204069 marker and the IA201502 marker in the 23rd linkage group of Strawberry Parental Line Nou-2 was found to be highly correlated with the rate of strains exhibiting anthracnose wilting or firing (%) in the genus *Fragaria*.

4. Development of PCR Base Marker

In this example, primers that amplify the IA202631 marker and the IA200826 marker by PCR were designed by selecting regions from the region between the IA204069 marker and the IA201502 marker in the 23rd linkage group of Strawberry Parental Line Nou-2.

(1) Preparation of Primer

With the use of the sequence assembly software (ATGC ver.6), primers that recognizes the sequences of the IA202631 marker and the IA200826 marker were prepared on the basis of the sequence information thereof. Specifically, CGGTTAACCCCTCCTAGAAAATC (IA202631F_2A: SEQ ID NO: 24) and TGCAGCTGTGAGGTTGTCTTTAT (IA202631R_111A: SEQ ID NO: 25) were designed for IA202631, and CTGCAGAAAAGGGAGAAGAAGTTC (IA200826F_1A: SEQ ID NO: 26) and GCCAGATGAAATAGAAGATTAGCACC (IA200826R_259A: SEQ ID NO: 27) were designed for IA200826.

With the use of the sequence assembly software (ATGC ver.6), similarly, primers that recognizes the sequences of Specifically, GCTACTCATAGTAGGTCGATTGGAAG (SEQ ID NO: 28) and CTGCAGTTTACATGCAGCAGA (SEQ ID NO: 29) were designed for IA202531, and AAGTTCAACATTATCAAGGAAAATGAA (SEQ ID NO: 30) and AATTGATAACTATTAACAGCAGTCAGG (SEQ ID NO: 31) were designed for IA200064.

(2) Amplification by PCR

Figure 15:
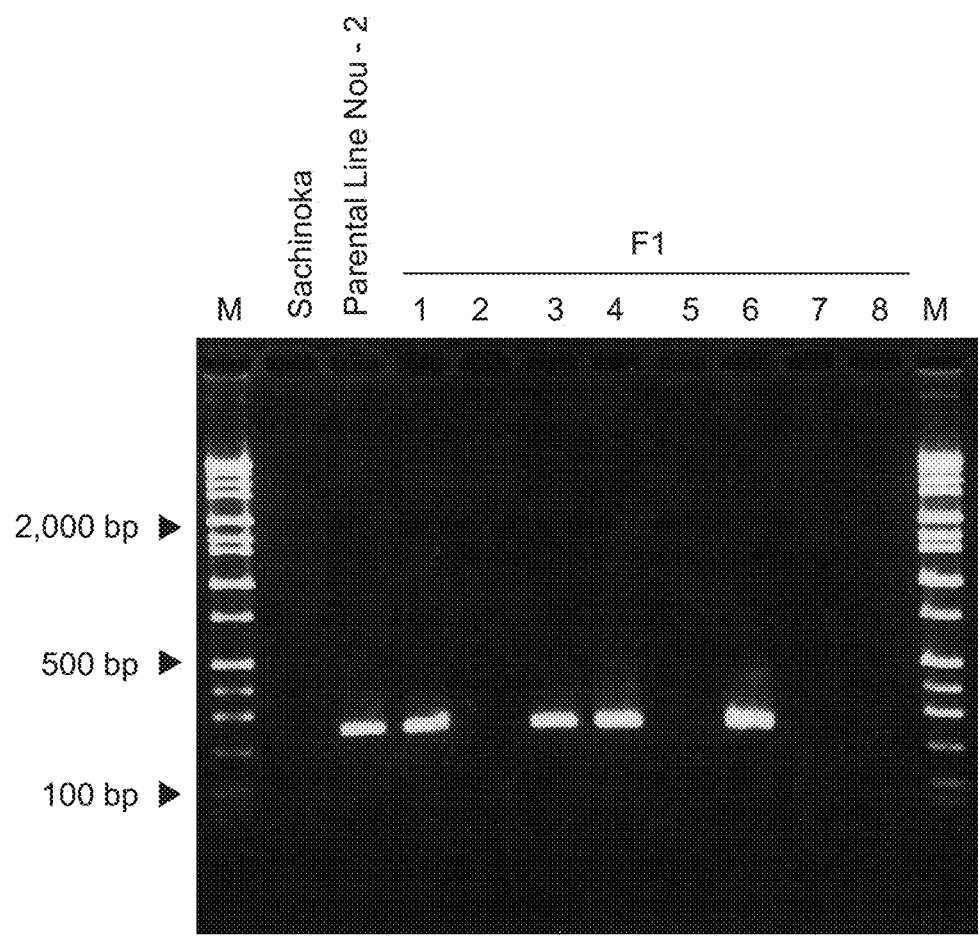
FIG. 15 is an electrophoretic photograph showing the results of amplification of the IA200826 marker via PCR.
Figure 16:
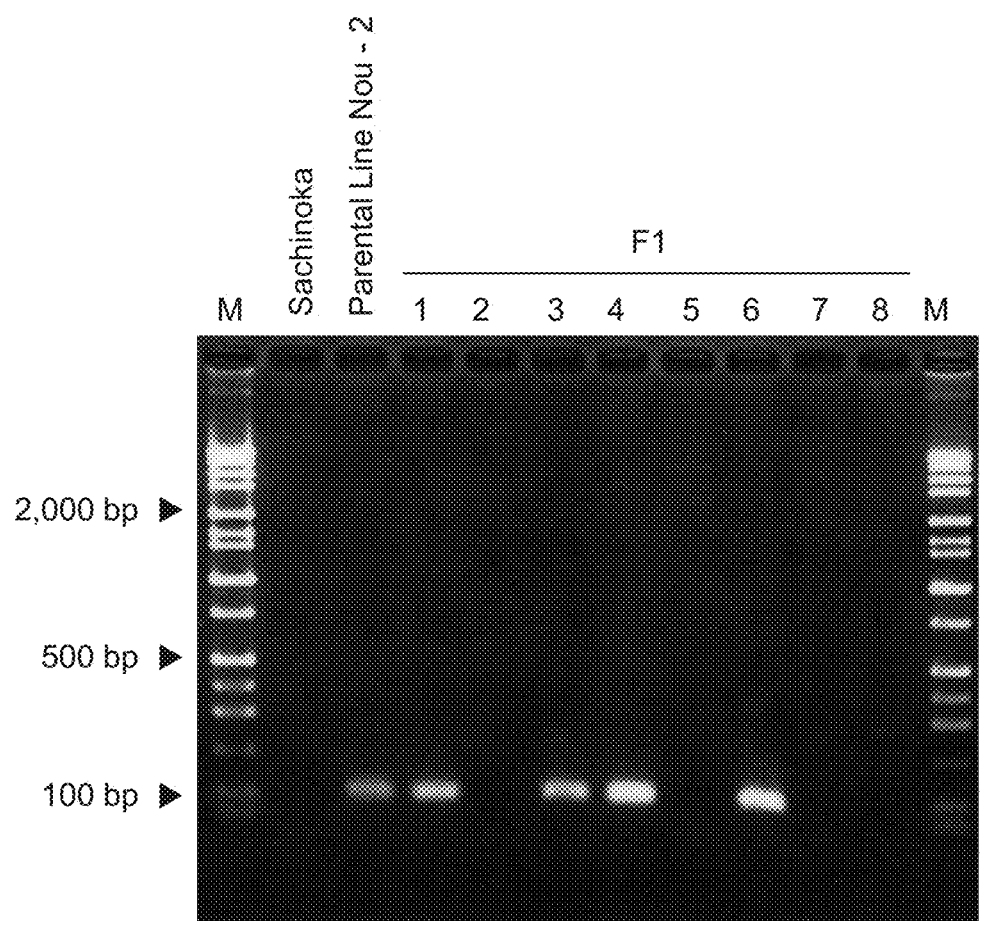
FIG. 16 is an electrophoretic photograph showing the results of amplification of the IA202631 marker via PCR.

The above pair of the primers and Taq polymerase (0.5 units, PrimeSTAR, Takara Bio Inc.) were added to the genomic DNA (15 ng) of the strawberry cultivar Sachinoka, Strawberry Parental Line Nou-2, and the hybrid progeny line 12, and the genomic DNA was amplified by PCR (30 cycles of 98° C. for 10 seconds, 55° C. for 5 seconds, and 72° C. for 1 minute, treatment at 72° C. for 3 minutes, followed by storage at 4° C.). The PCR-amplified DNA fragment was confirmed via electrophoresis (2.0% agarose gel, TAE, 100 V, 30 minutes). FIG. 15 shows the results of amplification of the IA200826 marker by PCR and FIG. 16 shows the results of amplification of the IA202631 marker by PCR. As shown in FIG. 15 and FIG. 16, all pairs of primers were found to be capable of amplifying the regions indicating the band patterns of interest in accordance with the signal data shown in FIG. 22.

Figure 20:
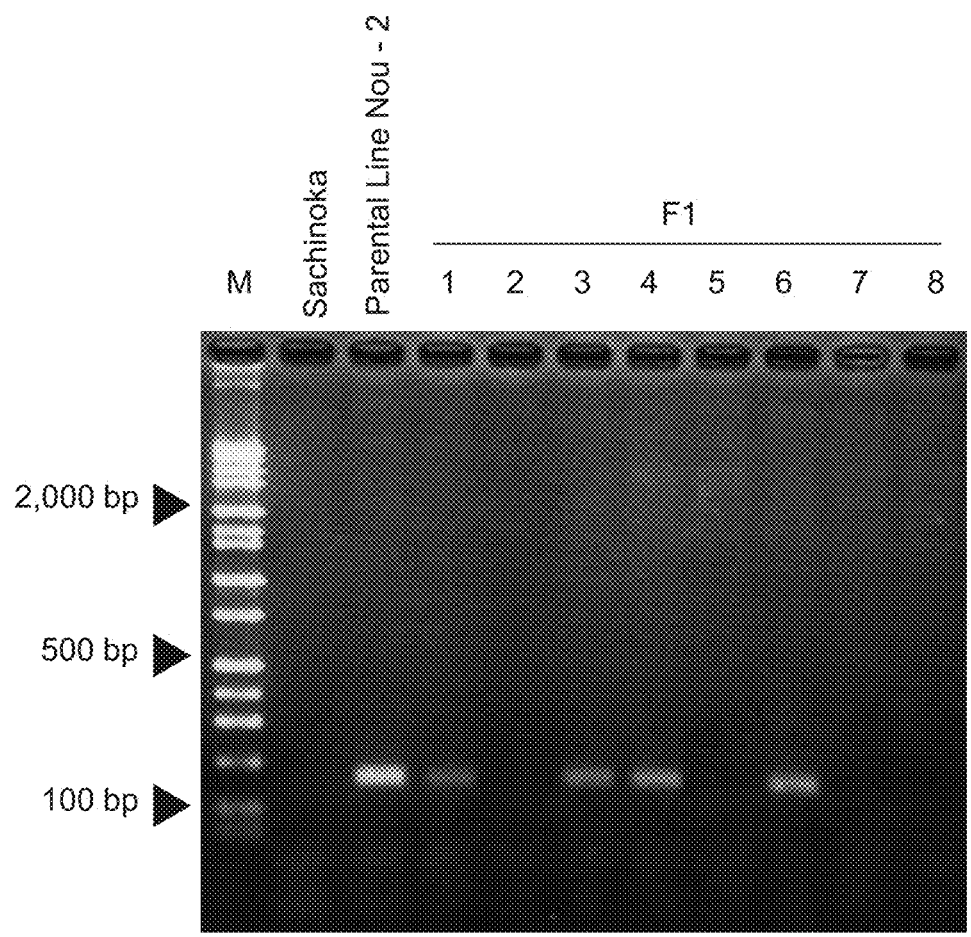
FIG. 20 is an electrophoretic photograph showing the results of amplification of the IA202531 marker via PCR.

FIG. 20 shows the results of amplification of the IA202531 marker by PCR. As shown in FIG. 20, the IA202531 marker was found to be capable of amplifying the region indicating the band pattern of interest with the aid of the pairs of the primers designed as described above in accordance with the signal data shown in FIG. 22.

Meanwhile, after PCR was carried out using genomic DNA of the strawberry cultivar Sachinoka and that of Strawberry Parental Line Nou-2 as the templates, the DNA fragment of the IA200064 marker amplified by PCR was subjected to sequencing by the Sanger's method. As a result, the sequence information as shown in SEQ ID NO: 32 was acquired from the genome of Sachinoka, and the sequence information as shown in SEQ ID NO: 32 and the sequence information as shown in SEQ ID NO: 4 were acquired from the genome of Parental Line Nou-2. The position 257 in SEQ ID NO: 32 and that in SEQ ID NO: 4 were found to be SNPs ("A" in SEQ ID NO: 32 and "T" in SEQ ID NO: 4). In SEQ ID NO: 32, 6 nucleotides from "A" at position 257 (i.e., ATGCAT) were the same as the residues constituting the recognition sequence of the NsiI restriction enzyme (i.e., ATGCAT).

Figure 21:
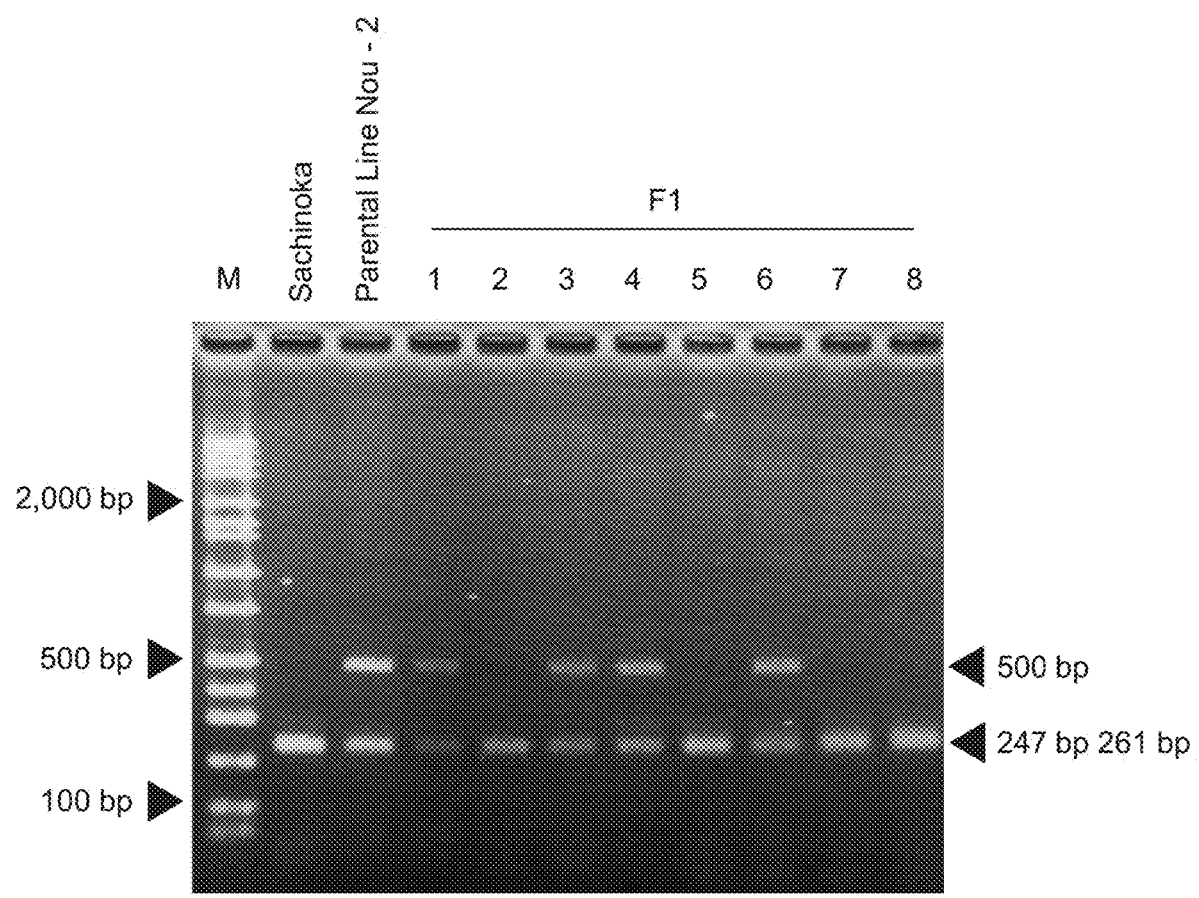
FIG. 21 is an electrophoretic photograph showing the results of amplification of the IA200064 marker via PCR and treatment thereof with restriction enzymes.

The IA200064 marker was amplified by PCR in the same manner as with other markers, NsiI (2 units, NEB) was added to the DNA fragment amplified by PCR, and the resultant was then treated at 37° C. for 1 hour. The DNA fragment treated with the restriction enzyme was confirmed via electrophoresis (2.0% agarose gel, TAE, 100 V, 30 minutes). FIG. 21 shows the results of amplification of the IA200064 marker by PCR, followed by treatment with the restriction enzyme. In the case of the cultivar Sachinoka having the restriction enzyme recognition site, bands were observed in the vicinity of nucleotides 247 and 261. In contrast, a band was observed in the vicinity of nucleotide 500 in addition to the bands in the vicinity of nucleotides 247 and 261 in the Parental Line Nou-2. As shown in FIG. 21, the band observed in the vicinity of nucleotide 500 was consistent with the signal data shown in FIG. 22. This indicates that a region indicating a band pattern of interest can be amplified with the use of the pair of primers designed as described above.

Figure 17:
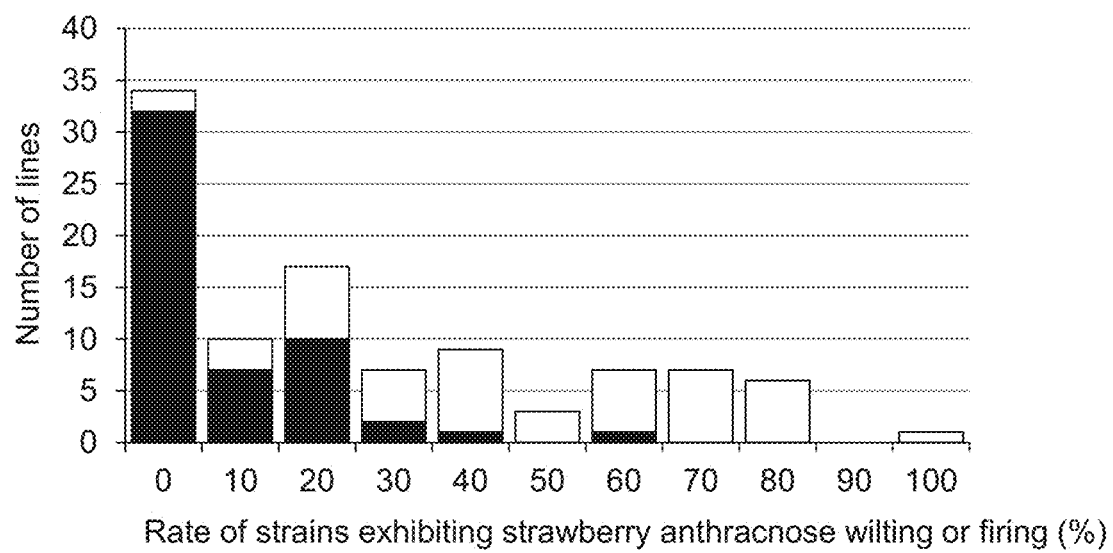
FIG. 17 is a characteristic diagram showing a comparison of the data concerning anthracnose resistance shown in FIG. 3 and the genotype data of the IA200826 marker.

5. Selection of Anthracnose Resistant Line (1) Genotype Data and Rate of Lines Exhibiting Anthracnose Wilting or Firing The genotype data for the IA200826 selection marker of the strawberry cultivar Sachinoka, Strawberry Parental Line Nou-2, and the 133 hybrid progeny lines were compared with the rates of lines exhibiting anthracnose wilting or firing (FIG. 17). Many lines that were excellent in terms of strawberry anthracnose resistance were found to have the IA200826 selection markers (10.6% on average). In contrast, many lines that were susceptible to strawberry anthracnose did not have the IA200826 selection markers (49.8% on average). As a result of the T test, significant differences were observed in both average values at the significance level of 1%.

(2) Selection of Unknown Line

I. Extraction of Genomic DNA

Separately, genomic DNA was extracted from the two hybrid progeny lines (A and B) of the strawberry cultivar Sachinoka and Strawberry Parental Line Nou-2 by the CTAB method.

II. Test with Selection Marker

Figure 18:
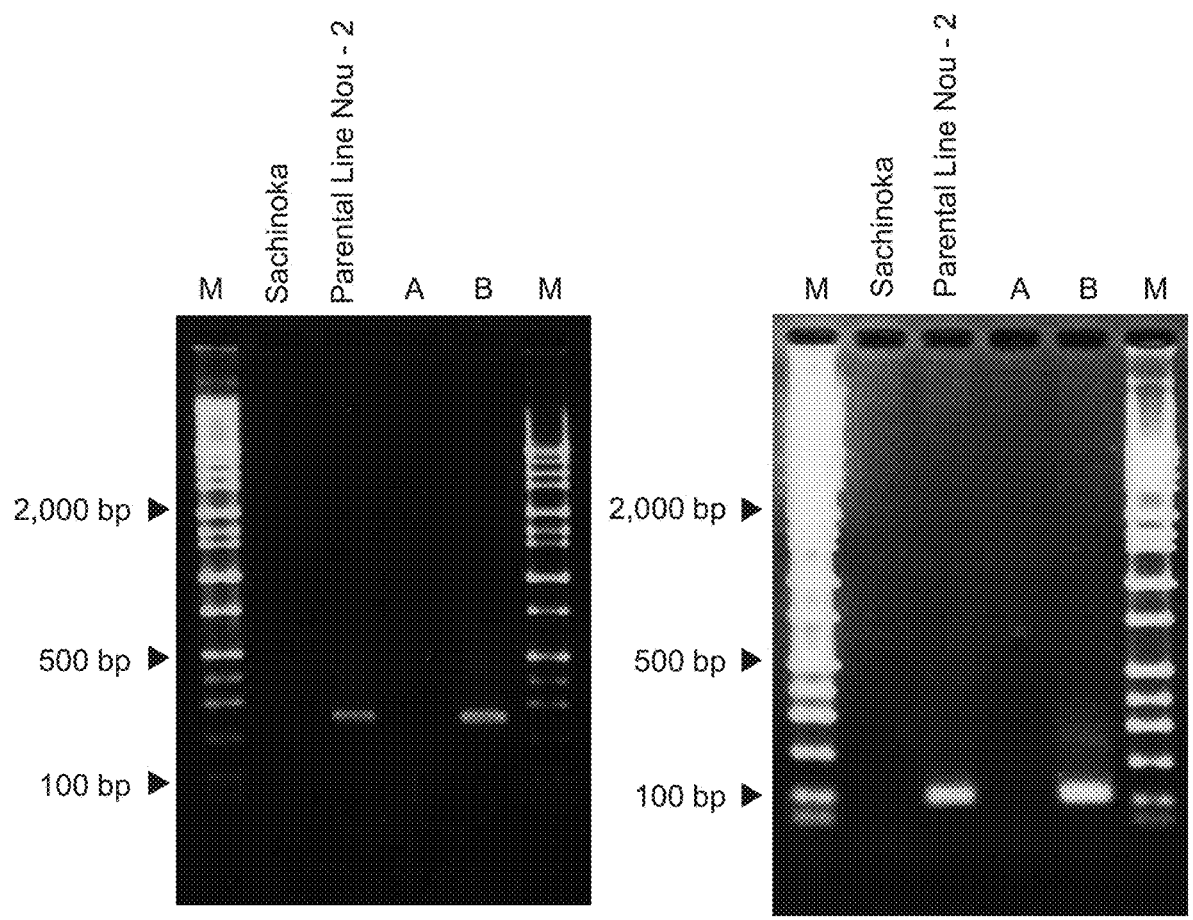
FIG. 18 is an electrophoretic photograph showing the results of amplification of the IA202631 marker and the IA200826 marker via PCR in the strawberry cultivar Sachinoka, the Strawberry Parental Line Nou-2, and two hybrid progeny lines (A and B).

The IA202631 primer pair (IA202631F_2A and IA202631R_111A) or the IA200826 primer pair (IA200826F_1A and IA200826R_259A) designed in 4. above and Taq polymerase (0.5 units, PrimeSTAR, Takara Bio Inc.) were added to genomic DNA (15 ng) of the strawberry cultivar Sachinoka, Strawberry Parental Line Nou-2, and the two hybrid progeny lines (A and B). The resultants were amplified by PCR (30 cycles of 98° C. for 10 seconds, 55° C. for 5 seconds, and 72° C. for 1 minute, treatment at 72° C. for 3 minutes, followed by storage at 4° C.). The DNA fragment amplified by PCR was confirmed via electrophoresis (2.0% agarose gel, TAE, 100 V, 30 minutes). FIG. 18 shows the results of amplification. As shown in FIG. 18, the hybrid progeny line A did not have either the IA202631 marker or the IA200826 marker. In contrast, the hybrid progeny line B had both the IA202631 marker and the IA200826 marker.

III. Comparison with the Data of Anthracnose Test

As a result of the anthracnose test, the hybrid progeny line A and the hybrid progeny line B exhibited the rates of lines exhibiting anthracnose wilting or firing of 80.0% and 13.3%, respectively. As a result of the T test, significant differences were observed in the rates of lines exhibiting anthracnose wilting or firing between the hybrid progeny line A and the hybrid progeny line B at the significance level of 1%. While the hybrid progeny line B comprising the IA202631 marker and the IA200826 marker exhibited a low rate of lines exhibiting anthracnose wilting or firing and excellent strawberry anthracnose resistance. The hybrid progeny line A without the IA202631 marker and the IA200826 marker exhibited a high rate of lines exhibiting anthracnose wilting or firing and poor strawberry anthracnose resistance. On the basis of the results demonstrated above, the use of such markers was found to enable identification of lines with excellent anthracnose resistance and lines with poor anthracnose resistance.

IV. PCR Amplification in Region Between Markers

Figure 19:
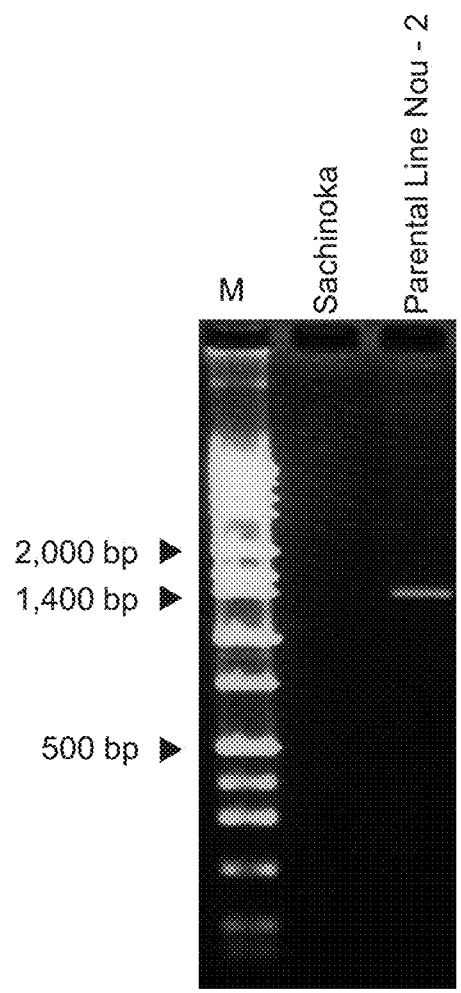
FIG. 19 is an electrophoretic photograph showing the results of amplification of a region comprising the IA202631 marker and the IA200826 marker via PCR in the strawberry cultivar Sachinoka, the Strawberry Parental Line Nou-2, and two hybrid progeny lines (A and B).

A pair of primers (IA200826F_1 A and IA202631R_111A) and Taq polymerase (0.5 units, PrimeSTAR, Takara Bio Inc.) were added to genomic DNA (15 ng) of the strawberry cultivar Sachinoka and Strawberry Parental Line Nou-2. The resultants were amplified by PCR (25 cycles of 98° C. for 10 seconds, 55° C. for 5 seconds, and 72° C. for 2 minutes, treatment at 72° C. for 3 minutes, followed by storage at 4° C.). The DNA fragment amplified by PCR was confirmed via electrophoresis (2.0% agarose gel, TAE, 100 V, 30 minutes). FIG. 19 shows the results of amplification. As shown in FIG. 19, a 1.4-kbp PCR-amplified DNA fragment was detected in Strawberry Parental Line Nou-2. That is, a region comprising the IA202631 marker and the IA200826 marker was amplified by PCR from the regions from the IA204069 to IA201502 markers in the 23rd linkage group of Strawberry Parental Line Nou-2.

The results described above demonstrate that a plurality of markers can be amplified with the use of a pair of primers from the regions from the IA204069 to IA201502 markers in the 23rd linkage group of Strawberry Parental Line Nou-2 and anthracnose of plants of the genus *Fragaria* can be identified.

All publications, patents, and patent applications cited herein are incorporated herein by reference in their entirety.

The invention claimed is:

1. A method for producing a *Fragaria* x *ananassa* plant line with improved anthracnose resistance, said method comprising:

producing progeny plants by crossing, wherein at least one parent of said progeny plants is a *Fragaria* x *ananassa* plant, and wherein said crossing is a sibling cross, a backcross, or a cross to produce a hybrid line;

extracting genomic DNA from at least one of said progeny plants; and analyzing said genomic DNA to detect the presence of a marker associated with anthracnose resistance in the extracted genomic DNA, and selecting a progeny line with the marker in its genome, thereby producing a *Fragaria* x *ananassa* plant line with improved anthracnose resistance, wherein said marker comprises at least 30 continuous nucleotides of the nucleotide sequence of SEQ ID NO: 8.

2. The method according to claim 1, wherein the analyzing comprises conducting a nucleic acid amplification reaction using a primer that specifically amplifies the marker associated with anthracnose resistance in the *Fragaria* x *ananassa* plant to determine the presence of the marker associated with anthracnose resistance in the *Fragaria* x *ananassa* plant.

3. The method according to claim 1, wherein the analyzing involves the use of a DNA chip comprising a probe corresponding to the marker associated with anthracnose resistance in the *Fragaria* x *ananassa* plant.

4. The method according to claim 1, wherein the progeny plant is a seed or seedling and the genomic DNA is extracted from the seed or seedling.

5. A method for producing a *Fragaria* x *ananassa* plant line with improved anthracnose resistance, said method comprising:
- extracting genomic DNA from at least one *Fragaria* x *ananassa* plant;
- analyzing said genomic DNA to detect the presence of a marker associated with anthracnose resistance in the extracted genomic DNA, and selecting a *Fragaria* x *ananassa* plant with the marker in its genome, thereby selecting a *Fragaria* x *ananassa* plant with improved anthracnose resistance; and
- using the selected plant as a parent plant for crossing, to thereby produce progeny plant(s) containing said marker, wherein said crossing is a sibling cross, a backcross, or a cross to produce a hybrid line,
- wherein said marker comprises at least 30 continuous nucleotides of the nucleotide sequence of SEQ ID NO: 8.

\* \* \* \* \*